United States Patent
Moller et al.

(10) Patent No.: US 6,524,827 B2
(45) Date of Patent: Feb. 25, 2003

(54) 2,6-β-D-FRUCTAN HYDROLASE ENZYME AND PROCESSES FOR USING THE ENZYME

(75) Inventors: Soren Moller, Holte (DK); Charlotte Johansen, Holte (DK); Thomas Schafer, Farum (DK); Peter Rahbek Ostergaard, Virum (DK); Lisbeth Hedegaard Hoeck, Skodsborg (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/969,362

(22) Filed: Oct. 2, 2001

(65) Prior Publication Data

US 2002/0076790 A1 Jun. 20, 2002

Related U.S. Application Data

(62) Division of application No. 09/397,885, filed on Sep. 17, 1999, now Pat. No. 6,323,007.
(60) Provisional application No. 60/101,615, filed on Sep. 24, 1998, and provisional application No. 60/111,675, filed on Dec. 10, 1998.

(30) Foreign Application Priority Data

Sep. 18, 1998 (DK) .......................................... 1998 01173
Dec. 9, 1998 (DK) .......................................... 1998 01623

(51) Int. Cl.$^7$ .................................................. C12N 9/24
(52) U.S. Cl. ...................... 435/74; 435/183; 435/252.3; 435/252.33; 435/320.1; 536/23.2
(58) Field of Search ................................ 435/183, 200, 435/252.3, 252.33, 320.1; 536/23.2

(56) References Cited

FOREIGN PATENT DOCUMENTS

WO     WO 99/31020     6/1999

OTHER PUBLICATIONS

Miasnikov, FEMS Microbiology Letters, vol., 154, pp. 23–28 (1997).
Bezzate et al., Journal of Bacteriology, vol. 176, No. 8, pp. 2177–2183, (Apr. 1994).

*Primary Examiner*—Ponnathapu Achutamurthy
*Assistant Examiner*—Christian L. Fronda
(74) *Attorney, Agent, or Firm*—Elias Lambiris; Jason Garbell

(57) ABSTRACT

The present invention relates to isolated polypeptides having polypeptide having 2,6-β-D-fructan hydrolase activity and isolated nucleic acid sequences encoding the polypeptides. The invention also relates to nucleic acid constructs, vectors, and host cells comprising the nucleic acid sequences as well as methods for producing and using the polypeptides.

16 Claims, 8 Drawing Sheets

1)

2)

3)

4)

SEQUENCE LISTING

<160> NUMBER OF SEQ ID NOS: 15

<210> SEQ ID NO 1
<211> LENGTH: 923
<212> TYPE: PRT
<213> ORGANISM: Paenibacillus amylolyticus

<400> SEQUENCE: 1

```
Met Lys Asp Lys Ser Lys Phe Ala Ile Cys Leu Leu Met Ala Thr Gly
  1               5                  10                  15

Leu Thr Leu Thr Ser Asn Gly Ile Phe Thr Ser Lys Ser Ile Ala Ala
             20                  25                  30

Ser Ala Val Leu Ala Asp Gln Glu Thr Asn Lys Gln Ala Lys Glu Glu
         35                  40                  45

Leu Asp Ile Phe Glu Ser Ala Ser Lys Ser Asn Thr Asn Leu Ile Gly
     50                  55                  60

Trp Gln Val Lys Gly Lys Gly Leu Glu Asp Thr Ser Glu Gly Ile
 65                  70                  75                  80

Leu Leu Thr Ser Gln Pro Lys Glu Asn Val Met Ala Ile Ser Glu Thr
                 85                  90                  95

Val Ser Asp Asp Phe Ile Tyr Glu Ala Asp Val Met Ile Arg Asp Thr
            100                 105                 110

Lys Ala Asp Ala Thr Leu Leu Phe Arg Ser Asn Glu Asp Gly Phe Ser
        115                 120                 125

Ser Tyr Met Leu Gln Ile Val Pro Asp Ala Gly Leu Ile Arg Leu Arg
    130                 135                 140

Asp Ala Arg Thr Gly Asp Gly Lys Leu Lys Glu Arg Lys Val Ser
145                 150                 155                 160

Val Glu Met Gly Gln Ile Tyr His Leu Lys Val Lys Ala Val Gly Ser
                165                 170                 175

Ser Leu Lys Val Tyr Trp Gly Asn Gln Tyr Lys Pro Leu Ile Asp Val
            180                 185                 190

Gln Asp Ile Ser Tyr Gln Ser Gly Lys Leu Gly Leu His Val Trp Asp
        195                 200                 205

Gly Ser Ala Leu Phe Ser Asn Ile Val Val Ser Asp Leu Lys Gly Asn
    210                 215                 220

Leu Gly Thr Val Leu Ser Ser Lys Gly Lys Trp Gln Pro Asp Ile Asn
225                 230                 235                 240

Gly Lys Arg Gly Thr Val Glu Gln Gly Ser Ile Ala Gln Ile Tyr
                245                 250                 255

Asn Lys Glu Ala Thr Asp Met Val Tyr Glu Gly Asn Ile Thr Leu Arg
            260                 265                 270

Pro Asp Ser Ile Ala Ala Leu Ala Phe Arg Ser Ser Thr Asp Gly Ala
        275                 280                 285

Glu Gly Tyr Glu Ala Thr Leu Thr Lys Glu Gly Asp Gln Val Arg Val
    290                 295                 300

Ser Leu Thr Asn Thr Lys Gly Thr Val Ile Ala Ser Ser Gln Arg Thr
305                 310                 315                 320

Tyr Pro Ser Gln Met Gly Ala Lys His His Val Glu Ile Lys Ala Lys
                325                 330                 335

Gly Asp Arg Ile Gln Val Phe Leu Asp Gly Tyr Thr Thr Ala Ala Ile
            340                 345                 350

Asp Val Lys Asp Ser Thr Tyr Lys Ser Gly Ser Thr Gly Ile Val Val
```

```
                355                 360                 365
Lys Lys Gly Thr Ala Tyr Phe Gln Asp Thr Tyr Val Thr Glu Leu Ser
    370                 375                 380

Gln Tyr Tyr Asn Glu Ile Tyr Arg Pro Gln Tyr His Tyr Thr Pro Ile
385                 390                 395                 400

Arg Gly Ser Ala Ser Asp Pro Asn Gly Leu Val Tyr Phe Glu Gly Glu
                405                 410                 415

Tyr His Leu Phe His Gln Asp Gly Thr Trp Ala His Ala Val Ser
            420                 425                 430

Lys Asp Met Leu Asn Trp Lys Arg Leu Pro Ile Ala Leu Pro Trp Asn
            435                 440                 445

Asp His Gly His Val Trp Ser Gly Ser Ala Val Ala Asp Met Thr Asn
450                 455                 460

Ala Ser Gly Leu Phe Gly Asp Ser Gly Gly Lys Gly Leu Ile Ala Tyr
465                 470                 475                 480

Tyr Thr Ser Phe Asn Pro Asp Ser Pro Asn Gly Asn Gln Arg Ile Gly
                485                 490                 495

Leu Ala Tyr Ser Lys Asp Gln Gly Arg Thr Trp Glu Tyr Ser Lys Glu
                500                 505                 510

Arg Pro Ile Val Ile Glu Asn Pro Gly Lys Ser Gly Asn Glu Ala Gly
            515                 520                 525

Asn Trp Asp Phe Arg Asp Pro Lys Val Ile Arg Asp Glu Asn Asn
            530                 535                 540

Arg Trp Val Met Val Val Ser Gly Gly Asp His Ile Arg Phe Tyr Thr
545                 550                 555                 560

Ser Thr Asn Leu Leu Asp Trp Thr Leu Thr Asp Asn Trp Gly Tyr Gly
                565                 570                 575

Asp Tyr Val Arg Gly Gly Val Trp Glu Cys Pro Asp Leu Phe Gln Leu
            580                 585                 590

Pro Val Asp Gly Thr Ser Gln Lys Lys Trp Val Met Met Ile Ser Thr
            595                 600                 605

Gly Ala Asn Pro Lys Thr Gly Gly Ser Asp Ala Glu Tyr Phe Ile Gly
610                 615                 620

His Leu Thr Ala Asp Gly Lys Phe Val Asn Asp Asn Pro Ala Gly Lys
625                 630                 635                 640

Val Leu Arg Thr Asp Phe Gly Lys Glu Phe Tyr Ala Ser Met Ser Phe
                645                 650                 655

Ala Asn Met Pro Asp His Arg Thr Val Met Met Ala Trp Met Thr Asn
                660                 665                 670

Trp Asp Tyr Pro Phe Ala Phe Pro Thr Ser Asn Trp Lys Gly Glu Leu
            675                 680                 685

Thr Ile Pro Arg Glu Val Ser Leu Val Thr Thr Glu Asp Gly Ile Arg
690                 695                 700

Met Val Gln Ser Pro Ile Lys Glu Leu Glu Ser Leu Arg Lys Pro Leu
705                 710                 715                 720

Tyr Ser Ala Ser Asn Lys Ser Val Ser Pro Ser Ser Gly Asn Leu Leu
                725                 730                 735

Lys Gly Ile Ile Ser Gly Ala Tyr Glu Ile Glu Ala Glu Ile Glu Ile
            740                 745                 750

Pro Glu Thr Ser Thr Val Thr Glu Phe Gly Phe Asn Ile Arg Glu Gly
            755                 760                 765

Ala Asn Gln Lys Thr Val Val Gly Tyr Lys Ala Ser Asp Ser Arg Met
770                 775                 780
```

```
Phe Val Asp Arg Thr Ala Ser Gly Glu Thr Asp Phe Ser Asn Leu Phe
785                 790                 795                 800

Ser Lys Lys His Glu Ala Pro Thr Gln Met Glu Asn Asn Arg Ile Lys
                805                 810                 815

Met Arg Ile Leu Val Asp Glu Ser Ser Val Glu Ala Phe Gly Asn Asp
            820                 825                 830

Gly Lys Val Val Phe Ser Asp Val Ile Phe Pro Asp Pro Ala Ser Arg
        835                 840                 845

Ala Met Ser Phe Tyr Val Lys Gly Gly Asn Val Asn Val Val Ser Leu
    850                 855                 860

Lys Val His Gln Leu Gln Ser Val Trp Asn Ala Asp Ile Pro Ser Lys
865                 870                 875                 880

Val Gln Ile Lys Met Asp Thr Ser Val Arg Glu Leu Gly Val Gly Glu
                885                 890                 895

Ser Asp Thr Leu Gln Ala Met Val Glu Tyr Gly Pro Gly Leu Gly Val
            900                 905                 910

Gln Pro Leu Lys Trp Asn Pro Val Ile Thr Thr
        915                 920
```

<210> SEQ ID NO 2
<211> LENGTH: 2769
<212> TYPE: DNA
<213> ORGANISM: Paenibacillus amylolyticus

<400> SEQUENCE: 2

```
atgaaagata aatctaaatt cgcaatatgt cttctgatgg caacgggatt aactctgact      60
tcaaacggta ttttacatc taaatcaatt gcggctagtg ctgtacttgc tgatcaggaa     120
acaaataaac aggctaagga ggagcttgat attttgaaa gcgcatccaa gtcaaatacc     180
aatctgatag gctggcaagt gaaaggaaaa ggaggattag aggatacttc agaaggaatc     240
ttgctaactt cacagcctaa agaaaatgta atggccatct cagagacagt gtccgatgat     300
tttatctatg aagctgatgt catgatcagg gatacgaagg cagacgcaac attgttgttt     360
cgttctaatg aggatggctt agctcgtac atgctgcaaa tcgttccgga cgcaggtctg     420
attcggttaa gagatgcaag aactggagat gggaaattaa aggaggagcg taaagtttct     480
gttgaaatgg ggcaaatcta tcatctcaaa gtgaaggcag tgggttcctc gctaaaagta     540
tattggggca atcaatataa accattaatt gatgttcaag acatttcgta tcaaagcgga     600
aagcttggac tccatgtatg ggatggatcc gccttgtttt cgaacatcgt ggtgagcgat     660
ctgaaaggta atttgggtac ggtgctttct agcaagggaa aatggcagcc tgatatcaac     720
ggcaaaagag ggacggtaga acaggggagc atagcrcagc aaatctataa caaagaggcg     780
actgatatgg tctatgaagg gaatattacc cttcgtcctg attctattgc agctctcgca     840
tttcgatctt caaccgatgg agctgaagga tatgaagcta ctcttacgaa ggaaggagat     900
caggtccgtg taagtttgac gaatacaaaa ggaacagtaa ttgcaagttc gcaacgtact     960
tatccgagtc agatgggagc caaacatcat gtggaaatca aggcaaaggg agatcgaatt    1020
caggtcttcc tggacgggta cactacggcc gcgattgacg tgaaagattc aacctacaag    1080
agtggaagta ccggaatcgt cgtaaaaaag gggacggctt actttcagga tacttatgtg    1140
acggaactga gccaatatta caatgagata tatcgtccac aatatcacta cacgccaata    1200
cgtggttcag cgagtgatcc gaatggactt gtctacttcg aaggagaata tcatctcttc    1260
catcaggatg gaggaacatg ggcgcatgcg gtaagtaaag atatgctgaa ctggaaacgg    1320
```

-continued

```
cttccgattg cacttccctg gaatgatcac ggacatgtct ggtctgggtc ggctgttgcg      1380
gatatgacaa atgcatctgg tttattcgga gattcaggag gcaagggcct tattgcatac      1440
tatacttcct ttaatccgga tagcccgaat gggaaccagc gtataggtct agcttacagt      1500
aaagaccaag gtcgtacttg ggagtattcg aaggagcgcc cgattgtgat cgagaacccg      1560
ggtaagagcg gaaatgaagc tgggaattgg gatttccgcg atccgaaagt aatccgtgat      1620
gatgagaata accgatgggt tatggttgtg tccggaggag atcatattcg tttctatact      1680
tcaacaaatt tacttgactg gacattgaca gataattggg gatatgggga ttacgtccgc      1740
ggaggagtat gggaatgccc tgatttgttc cagcttccgg tagacggaac gtcacagaaa      1800
aagtgggtta tgatgatcag tacaggagcg aatcccaaaa caggcggatc agatgccgag      1860
tattttatcg gtcatttaac agctgatggt aaattcgtaa cgataatcc ggcaggtaag       1920 gtgttaagaa cagattttgg taaagaattt tacgcttcga tgtcttttgc taacatgcct      1980
gatcatcgca cagtgatgat ggcgtggatg acgaattggg attatccgtt cgctttccca      2040
acgtccaatt ggaaaggtga actaaccatt ccgagagaag tatcattggt aacgaccgaa      2100
gatggaattc ggatggtgca aagtccaatc aaagaattgg aatcactgcg taaacctttg      2160
tattctgctt ctaacaagtc ggtgagccct tcttccggga atctgctaaa aggtattatt      2220
tcaggtgctt acgaaattga agctgaaatt gaaatccctg aaaccagcac agtgaccgag      2280
tttggcttta acattcgtga gggtgcaaat cagaagacgg tcgtgggtta taaggcaagc      2340
gatagtcgta tgtttgtgga ccgaactgca tccggtgaaa cggattttc taacctttc       2400 agtaagaaac atgaagcgcc tacgcaaatg gagaataatc ggatcaagat gcgtattctt      2460
gtggatgagt cttctgttga agcctttggt aacgacggca aagtcgtctt ttcagatgtt      2520
atatttccgg atcctgctag tagagcgatg agttttttacg taaaaggcgg gaatgtgaat      2580
gttgtttcct tgaaagtgca tcaacttcaa tctgtctgga atgcggacat tccttcaaaa      2640
gttcaaataa agatggatac gagcgttcgg gaactggggg taggcgagtc ggatacactg      2700
caggcgatgg tcgagtatgg cccgggtcta ggcgttcaac cgcttaagtg gaatccagta      2760
ataacgacg                                                             2769
```

<210> SEQ ID NO 3
<211> LENGTH: 1277
<212> TYPE: PRT
<213> ORGANISM: Paenibacillus pabuli

<400> SEQUENCE: 3

```
Met Lys Phe Ile Phe Arg Ser Ile Gly Cys Val Leu Leu Ser Cys Val
  1               5                  10                  15

Leu Gly Ser Ser Ala Ala Gly Ala Tyr Ser Thr Ala Ser Val Met Glu
             20                  25                  30

Thr Asn Glu Ser Gln Arg Met Glu Gln Thr Ser Lys Glu Ser Ala Lys
         35                  40                  45

Gln Gly Glu Ala Val Arg Met Leu Thr Lys Val Ser Lys Ala Val Thr
     50                  55                  60

Asn Leu Ser Asp Trp Thr Leu Gln Gly Arg Gly Ser Leu Glu Asp Thr
 65                  70                  75                  80

Asp Glu Gly Leu His Leu Ala Ser Glu Ala Arg Glu Asn Val Met Ala
                 85                  90                  95

Leu Ser Ala Thr Arg Ala Asp Asn Phe Ile Tyr Glu Ala Asp Leu Met
            100                 105                 110
```

-continued

```
Ile Gln Asp Met Lys Ala Asp Thr Ser Leu Val Phe Arg Ser Asn Asp
            115                 120                 125
Thr Gly Trp Ser Ser Tyr Met Leu Gln Val Val Pro Gln Ala Gly Val
        130                 135                 140
Ile Arg Leu Arg Asp Ala Ser Gly Gln Pro Gly Thr Leu Asn Val Glu
145                 150                 155                 160
His Lys Ala Asn Leu Glu Ser Gly Gly Ile Tyr His Leu Lys Val Lys
                165                 170                 175
Ala Asp Gly Glu Ser Leu Gln Val Tyr Trp Asp Asn Arg Tyr Asp Pro
            180                 185                 190
Val Ile Asp Val Lys Asp Ser Ala Tyr Ser Ser Gly Arg Leu Gly Leu
        195                 200                 205
His Val Trp Asp Gly Ser Ala Leu Phe Gln Asn Val Gln Val Ser Ile
    210                 215                 220
Met Asn Gly Asn Ile Gly Lys Pro Ile Ser Ser Val Gly Glu Trp Gln
225                 230                 235                 240
Pro Asp Leu Lys Gly Tyr Lys Gly Lys Gly Asn Ala Gln Gly Lys Gly
                245                 250                 255
Gln Ile Val Tyr Glu Lys Ala Ala Ser Asp Phe Val Tyr Glu Gly Asn
            260                 265                 270
Leu Tyr Leu Ala Asp Ala Ser Thr Ser Ala Ala Leu Leu Phe Arg Ala
        275                 280                 285
Ser Thr Asp Gly Thr Lys Gly Tyr Glu Ala Ala Leu Ile Arg Glu Gly
    290                 295                 300
Glu Glu Val Arg Val Gln Leu Arg Lys Ala Asp Gly Thr Val Leu Ala
305                 310                 315                 320
Ser Ser Asn Arg Lys Val Pro Ser Gln Pro Gly Ala Arg His His Ile
                325                 330                 335
Glu Val Ile Ala Ser Gly Ser Leu Ile Gln Val Tyr Val Asp Gly Tyr
            340                 345                 350
Thr Pro Ala Ala Val Glu Val Thr Asp Lys Ser Tyr Ala Lys Gly Asn
        355                 360                 365
Ala Gly Leu Val Val Gln Gln Gly Met Ala Tyr Phe Gln Asp Ile Tyr
    370                 375                 380
Met Thr Glu Glu Ser Met Tyr Tyr Lys Glu Asn Tyr Arg Pro Gln Tyr
385                 390                 395                 400
His Tyr Ser Pro Leu Arg Gly Ser Ala Ser Asp Pro Asn Gly Leu Val
                405                 410                 415
Tyr Tyr Glu Gly Glu Tyr His Leu Phe His Gln Asp Gly Gly Thr Trp
            420                 425                 430
Ala His Ala Val Ser Ser Asp Leu Ile Asn Trp Lys Arg Leu Pro Ile
        435                 440                 445
Ala Leu Pro Trp Asn Asp Gln Gly His Val Trp Ser Gly Ser Ala Ile
    450                 455                 460
Ala Asp Leu Asn Asn Ala Ser Gly Leu Phe Thr Asp Ser Gly Gly Lys
465                 470                 475                 480
Gly Leu Ile Ala Tyr Tyr Thr Ser Tyr His Pro Asp Lys Pro Gly Gly
                485                 490                 495
Asn Gln Arg Ile Gly Leu Ala Tyr Ser Thr Asp Gln Gly Arg Asn Trp
            500                 505                 510
Gln Tyr Ala Lys Glu Arg Pro Ile Val Ile Asp Asn Pro Gly Lys Asn
        515                 520                 525
```

```
Gly Asp Asp Pro Gly Ser Trp Asp Phe Arg Asp Pro Lys Val Val Arg
    530                 535                 540
Asp Glu Asp His Asn Arg Trp Val Met Val Ser Gly Gly Asp His
545                 550                 555                 560
Ile Arg Phe Phe Thr Ser Thr Asn Leu Leu Asp Trp Thr Leu Thr Asp
                    565                 570                 575
Asn Phe Gly Tyr Gly Asp Tyr Val Arg Gly Val Trp Glu Cys Pro
            580                 585                 590
Asp Leu Ile Gln Leu Pro Val Asp Gly Thr Gly Gln Arg Lys Trp Val
                595                 600                 605
Leu Leu Ile Ser Thr Gly Ala Asn Pro Lys Thr Gln Gly Ser Asp Ala
    610                 615                 620
Glu Tyr Phe Val Gly Gln Leu Thr Ala Asp Gly Lys Phe Leu Asn Asp
625                 630                 635                 640
His Pro Ala Gly Gln Val Leu Arg Thr Asp Tyr Gly Lys Glu Phe Tyr
                645                 650                 655
Ala Ser Met Ser Phe Ala Asn Met Pro Asn Gln Arg Lys Val Met Leu
            660                 665                 670
Ala Trp Met Thr Asn Trp Asp Tyr Pro Phe Glu Phe Pro Thr Ser Ser
        675                 680                 685
Trp Lys Gly Gln Leu Thr Ile Pro Arg Glu Val Ser Leu Arg Thr Thr
    690                 695                 700
Asp Glu Gly Val Arg Leu Val Gln Thr Pro Ile Thr Glu Leu Gln Lys
705                 710                 715                 720
Leu Arg His Asn Leu Tyr Ser Ala Gln Gln Met Thr Val Gly Pro Lys
                725                 730                 735
Ser Lys Asn Pro Leu Glu Gly Leu Thr Ala Gly Ala Tyr Glu Ile Glu
            740                 745                 750
Ala Glu Val Glu Ile Pro Ala Asn Ser Ser Val Thr Glu Phe Gly Phe
        755                 760                 765
Gln Leu Arg Gln Arg Glu Gly Gln Lys Thr Thr Val Ala Tyr Arg Val
    770                 775                 780
Asp Thr Gln Asn Met Phe Val Asp Arg Thr Thr Ser Gly Asp Val Ser
785                 790                 795                 800
Phe Ser Asp Leu Phe Thr Lys Val His Glu Ala Ser Leu Lys Pro Glu
                805                 810                 815
Asn Gln Lys Val Lys Leu Arg Ile Phe Val Asp Glu Ser Ser Val Glu
            820                 825                 830
Val Phe Gly Asn Asp Gly Lys Val Val Phe Ser Asp Val Ile Phe Pro
        835                 840                 845
Asp Pro Ala Gly Arg Ala Met Ala Phe Tyr Ser Leu Gly Gly Glu Val
    850                 855                 860
Lys Val Ser Ser Met Lys Val Tyr Ala Leu Asp Asn Ile Trp Arg Lys
865                 870                 875                 880
Ser Thr Asp Ser Lys Met Gln Val Phe Ala Asp Met Gln Arg Arg Ile
                885                 890                 895
Val Asn Met Gly Gln Thr Gln Thr Leu Tyr Ala Thr Val Glu Gly Arg
            900                 905                 910
Ser Gly Lys Gly Ala Ala Gln Pro Val Lys Trp Lys Val Ser Asn Pro
        915                 920                 925
Lys Val Ala Gln Ile Val His Ser Asp Lys Thr Lys Ala Thr Val Arg
    930                 935                 940
Ala Val Gly Gly Gly Glu Ala Val Val Thr Val Ser Thr Thr Asp Gly
```

```
                945          950           955           960
Lys Ala Ser Ala Gln Ile Pro Met Lys Val Ser Ser Gly Val Phe His
                    965           970           975
Thr Asn Leu Ser Gly Trp Lys Ala Asp Lys Ser Ser Ala Gln Trp Leu
            980           985           990
Val Ser Glu Gln Gly Ile Gln Gly Gly Tyr Ser Gly Asp Thr Gln Tyr
            995          1000          1005
Ile Ala Gln Asp Thr Thr Ala Gly Asp Phe Gln Tyr Asp Ala Asp Leu
    1010          1015          1020
Thr Leu Gly Ala Gln Gly Gly Ala Gly Ser Ile Val Phe Arg Ala Ser
1025          1030          1035          1040
Glu Asp Gly Arg Ser Gly Tyr Tyr Leu Asn Ile Asp Pro Asn Leu Lys
            1045          1050          1055
Ser Ile Arg Leu Phe Tyr Lys Val Asn Gly Lys Phe Glu Asn Arg Gln
            1060          1065          1070
Val Leu Ala Gln Ile Pro Arg Phe Ile Arg Lys Asp His Met Tyr His
        1075          1080          1085
Ile Gln Ile Gln Ala Asn Gly Pro Arg Ile Gln Val Gly Val Asp Gly
    1090          1095          1100
Glu Arg Ile Ile Asp Leu Gln Asp Gly Thr Phe Ala Glu Gly His Phe
1105          1110          1115          1120
Gly Ile His Val Phe Gly Gly Ser Ala Ser Phe Gln Asn Val Asn Ala
            1125          1130          1135
Ile His Thr Lys Lys Ala Glu Leu Asp Gln Ile Ile Arg Asn Ala
        1140          1145          1150
Gly Ser Pro Val Ala Met Gln Ala Val Pro Ser Glu Ala Gly Glu Met
    1155          1160          1165
Ile Lys Val Ala Asp Glu Ala Glu Asn Ala Ser Glu Gly Phe Asn Trp
    1170          1175          1180
Val Leu Val Pro Thr Gly Asp Asp Ser Gly Ser Tyr Ser Ile Arg Thr
1185          1190          1195          1200
Leu Ser Gly Met Ser Leu Asp Trp Asp Val Gly Gln Asn Arg Ile Gln
            1205          1210          1215
Leu Tyr Ser Tyr Leu Gly Tyr Ala Asn Gln Arg Trp Asn Leu Ser Lys
            1220          1225          1230
Asn Glu Asp Gly Thr Met Arg Ile Thr Ser Ala His Asn Gly His Ala
            1235          1240          1245
Leu Gly Ile Ser Ala Ser Gly Pro Glu Leu Val Met Asp Glu Phe Arg
    1250          1255          1260
Gln Glu Asn Glu Tyr Gln Lys Trp Val Ile Lys Gln Gln
1265          1270          1275

<210> SEQ ID NO 4
<211> LENGTH: 3834
<212> TYPE: DNA
<213> ORGANISM: Paenibacillus pabuli

<400> SEQUENCE: 4
atgaaattca ttttccgatc catcggttgt gttctattat catgtgtcct aggtcttct      60 gctgctggag cctattccac agcatctgtt atggagacaa atgaatcgca aaggatggag    120
caaacctcca aggaatcagc aaaacaggga gaggcggttc gaatgttaac caaagtgtcg    180
aaggcagtta cgaatttgtc ggattggact ttgcaggta gaggcagtct ggaagatacg     240
gatgaaggac tccatctcgc ttcggaagcc agggagaatg tgatggccct atcagctaca    300
```

-continued

```
cgagctgata attttatcta tgaagctgat tgatgattc aggatatgaa agcggataca    360
agtcttgttt ttcgatccaa tgatacaggc tggtcttcat atatgctgca agtggttccc    420
caggctggtg tgatacgtct aagagatgcc agtggacagc cgggaacgtt aaatgtagaa    480
cataaagcaa acctggaatc tggaggtatc tatcatctga aagtgaaagc ggacggagag    540
agccttcagg tatattggga taatcgatac gacccggtga ttgatgtgaa agatagtgcc    600
tactcgtcag ggaggctggg gctccatgtg tgggatgggt cggctttgtt ccagaatgtg    660
caggtcagta tcatgaatgg caatatcggc aaaccgatta gcagcgtagg tgaatggcag    720
ccggatttga agggtataa agggaaagga acgctcagg gaaaaggaca gatcgtttac    780
gaaaaggcgg cttccgattt tgtgtatgaa gggaatctat atctggccga tgcgagtacc    840
tcagcggcgt tgctgttcag agcgagcaca gacgggacga agggatatga agcagccctg    900
atccgggaag gagaagaagt tcgggtacaa cttcgaaaag cggacggtac tgtgctcgca    960
agctcgaatc gtaaggttcc aagccaaccg ggagcgaggc atcacatcga agttattgcc   1020
tcgggcagct tgattcaggt ctatgtggat gggtacacgc tgcggctgt tgaggtcaca   1080 gataaaagct acgctaaagg aaatgctgga cttgtcgttc aacaaggcat ggcttatttt   1140
caggatattt tatgacaga agagtcgatg tactacaaag agaactaccg tcctcagtac   1200
cattattctc cgcttcgggg atcggcaagt gatccgaacg ggctggtcta ttatgaagga   1260
gaatatcatc tgtttcatca ggatggaggc acctgggctc atgcagtcag ttcggatctt   1320
ataaattgga agcgtttacc tattgctttg ccctggaatg atcagggtca tgtatggtca   1380
ggatcagcaa ttgcagatct gaataatgcc tctggtctgt tcacggattc gggcggaaaa   1440
ggtctgattg cgtactacac ttcctatcat ccggataaac ctggtggaaa tcagcgcatc   1500
ggccttgcct atagtaccga tcaaggccgg aattggcagt atgctaaaga acgtccgatt   1560
gtcattgata accctggcaa gaacggtgac gacccgggaa gctgggattt tcgtgatccg   1620
aaggtcgtcc gcgatgaaga ccataaccgc tgggtgatgg tggtgtccgg cggggatcac   1680
atccggttct ttacttccac caatctgctc gattggacct taaccgataa cttcggatat   1740
ggcgattacg ttcgtggcgg ggtgtgggag tgtcccgatc tgattcaact gcctgtagat   1800
ggaacgggtc aacgtaagtg ggtgcttctg atcagtacag gggccaatcc gaaaactcag   1860
ggatctgatg cggaatattt tgtaggtcag ctaactgctg atgggaaatt cctgaacgat   1920
catccggctg ggcaggtgtt gagaacggac tacggtaagg agttctacgc atcaatgtcc   1980
tttgcgaata tgccgaacca gcggaaagtt atgcttgcgt ggatgacgaa ctgggattat   2040
ccgtttgaat tcccaacctc ctcatggaaa ggacaactga ccataccgag agaagtctct   2100
cttcgaacca cggatgaagg cgtgcgtttg gtgcaaacac caatcactga gcttcagaaa   2160
ctgcggcata acctatacag tgcacaacaa atgacggttg gcccaaaatc aaaaaatccg   2220
ctggagggcc taacggcggg agcgtatgag attgaagctg aagtggaaat tccggctaac   2280
agttctgtaa ccgagtttgg ttttcaactg cgtcagagag aggggcagaa aaccactgta   2340
gcatacagag tggatacgca gaacatgttc gtggatcgca ccacctcagg tgacgtaagc   2400
ttctccgact tattcaccaa ggtccatgaa gcctcgttaa aacctgaaaa tcaaaaggtg   2460
aaactgcgca tatttgtcga tgaatcctct gttgaggtct ttggcaatga tggcaaggtt   2520
gttttctcgg atgtcatttt tcccgatccg gcgggcaggg cgatggcatt ctatagcctt   2580
ggtggggaag tgaaggtcag ctccatgaag gtgtacgcct tggacaatat ctggagaaag   2640
```

-continued

```
agcacggact ccaagatgca ggttttttgca gatatgcaaa aagaatagt gaatatgggg    2700 cagacgcaaa cgctgtacgc cacggtggaa ggcagatcag gtaaaggtgc cgctcaaccg    2760
gttaaatgga aggtaagcaa tcctaaagtg gcgcaaatcg ttcattctga taaaacgaaa    2820
gcaaccgttc gtgccgtggg tggaggcgaa gctgtagtaa ccgtatcgac gacagacggc    2880
aaagcttctg cccaaatacc gatgaaggta tccagcgggg tattccacac caacttatct    2940
ggctggaagg cagataaatc atctgcccaa tggcttgttt ccgaacaagg catacagggg    3000
gggtatagtg gagatacaca gtatatcgca caggatacta cggcagggga ttttcaatat    3060
gatgctgacc tgacgctggg agcacagggg ggagcggggt ctattgtatt ccgtgccagc    3120
gaggatggac gaagcggcta ctacttgaat atcgatccta acctgaagtc cattcgactg    3180
ttttataaag taaatggaaa attcgagaat cggcaggtgc tcgctcaaat ccctagattc    3240
attcgtaagg atcatatgta tcacattcaa attcaggcga acggtcctcg aatccaggtt    3300
ggtgtggacg gtgagcgaat aatagatctt caggatggga cgtttgctga aggacatttc    3360
ggtatccatg tgtttggcgg gagtgcttcc ttccagaatg tgaatgcaat ccatacgaag    3420
aaggcagaat tggaccagat cattattcgt aacgcaggaa gtcctgttgc aatgcaggct    3480
gttccatctg aagcaggaga aatgataaag gttgctgacg aggcagagaa tgcaagtgaa    3540
ggcttcaact gggtacttgt accgacaggg gatgattccg gctcttactc cattcggacc    3600
ttgagcggca tgtctcttga ttgggatgta ggacagaatc gcattcagct ctattcgtat    3660
cttggttatg cgaatcaacg ctggaacctt tcgaagaatg aggatggaac gatgcgcatc    3720
acaagtgcac ataacgggca cgcacttggt atatctgcga gtgggccaga actggtaatg    3780
gatgagtttc gtcaagaaaa cgagtatcaa aagtgggtta ttaagcaaca ataa          3834
```

<210> SEQ ID NO 5
<211> LENGTH: 943
<212> TYPE: PRT
<213> ORGANISM: Paenibacillus macerans

<400> SEQUENCE: 5

```
Met Gly Lys Gly Lys Ser Val Leu Ser Ile Leu Leu Ser Ser Ala Leu
  1               5                  10                  15

Ile Phe Ala Gly Leu Asp Ala Gly Met Val Arg Ala Ala Gly Ala Glu
             20                  25                  30

Thr Glu Thr Gly Lys Gly Ala Lys Ala Ile Phe Glu Ser Ala Thr Lys
         35                  40                  45

Leu Glu Thr Asn Leu Thr Gly Trp Arg Ile Glu Gly Lys Gly Arg Met
     50                  55                  60

Glu Thr Val Glu Gln Gly Leu Leu Val Ser Glu Pro Arg Glu Asn
 65                  70                  75                  80

Val Met Ala Leu Thr Glu Thr Arg Ala Ala Asp Phe Ile Tyr Glu Ala
                 85                  90                  95

Asp Val Met Val Thr Glu Arg Gln Ala Asp Ala Thr Leu Val Phe Arg
            100                 105                 110

Ser Asn Gln Asp Gly Trp Ser Ser Tyr Met Leu Gln Leu Val Pro Asn
        115                 120                 125

Ala Gly Leu Ile Arg Leu Lys Asp Ala Ser Glu Asp Gly Lys Leu Arg
    130                 135                 140

Glu Glu Arg Arg Val Asp Leu Ala Glu Gly Glu Ile Tyr His Leu Lys
145                 150                 155                 160

Val Lys Ala Glu Gly Thr Arg Leu Gln Val Phe Trp Gly Asp Arg Tyr
```

-continued

```
                165                 170                 175
Lys Pro Leu Ile Asp Val His Asp Gly Ala Tyr Ala Ser Gly Tyr Leu
                180                 185                 190
Gly Leu Asn Val Trp Asp Gly Ser Ala Leu Phe Gln Asn Val Lys Val
                195                 200                 205
Ser Glu Leu Asn Ser Asn Leu Gly Ala Ala Ile Ala Ser Phe Gly Val
            210                 215                 220
Trp Gln Pro Asp Leu Arg Gly Glu Leu Gly Thr Ala Asp Gly Thr Gly
225                 230                 235                 240
Arg Ala Leu Arg Leu Tyr Gln Gly Ala Glu Arg Asp Leu Val Leu Glu
                245                 250                 255
Gly Asn Val Ser Phe Ala Ala Asp Gln Gly Glu Ala Gly Leu Arg Phe
            260                 265                 270
Arg Ala Asn Gly Gln Gly Thr Asp Gly Tyr Glu Ala Ala Leu Arg Lys
            275                 280                 285
Asp Gly Gly Gln Val Trp Ala Glu Leu Arg Lys Ala Asp Gly Arg Val
        290                 295                 300
Ile Ala Ala Ser Glu Arg Ala Tyr Pro Ser Ala Ser Lys Ala Arg His
305                 310                 315                 320
His Leu Glu Ile His Ala Leu Gly Ser Arg Ile Gln Val Tyr Val Asp
                325                 330                 335
Gly Tyr Ala Glu Pro Ala Val Asp Ala Val Asp Asn Ser Tyr Ala Asp
            340                 345                 350
Gly His Ala Gly Phe Ala Val Ser Gly Gly Ala Ala Tyr Phe Gln Asp
            355                 360                 365
Val Tyr Leu Thr Ala Ala Asn Asp Tyr Tyr Thr Glu Lys Tyr Arg Pro
        370                 375                 380
Asp Tyr His Tyr Ser Pro Ala Arg Gly Ser Ala Ser Asp Pro Asn Gly
385                 390                 395                 400
Leu Val Tyr Tyr Glu Gly Glu Tyr His Leu Phe His Gln Asp Gly Gly
                405                 410                 415
Thr Trp Ala His Ala Val Ser Thr Asp Leu Val His Trp Lys Arg Leu
            420                 425                 430
Pro Ile Ala Leu Pro Trp Asn Asp Leu Gly His Val Trp Ser Gly Ser
        435                 440                 445
Ala Val Ala Asp Leu His Asn Ala Ser Gly Leu Phe Ala Asp Ser Gly
    450                 455                 460
Gly Lys Gly Leu Ile Ala Tyr Tyr Thr Ser Tyr Asn Pro Asp Arg Pro
465                 470                 475                 480
Asn Gly Asn Gln Arg Ile Gly Leu Ala Tyr Ser Lys Asp Arg Gly Arg
                485                 490                 495
Thr Trp Glu Tyr Ala Ala Glu Arg Pro Ile Val Ile Glu Asn Pro Gly
            500                 505                 510
Lys Gln Gly Asp Asp Pro Gly Gly Trp Asp Phe Arg Asp Pro Lys Val
        515                 520                 525
Val Arg Asp Glu Glu His Asn Arg Trp Val Met Val Ser Gly Gly
    530                 535                 540
Asp His Ile Arg Phe Phe Thr Ser Thr Asn Leu Ile Asp Trp Thr Leu
545                 550                 555                 560
Thr Asp Ser Phe Gly Tyr Gly Ala Tyr Val Arg Gly Val Trp Glu
                565                 570                 575
Cys Pro Asp Leu Phe Gln Leu Ala Val Asp Asp Thr Gly Glu Lys Lys
            580                 585                 590
```

-continued

```
Trp Val Leu Met Ile Ser Thr Gly Ala Asn Pro Asn Thr Gln Gly Ser
            595                 600                 605

Ala Ala Glu Tyr Phe Ile Gly Glu Leu Thr Pro Glu Gly Lys Phe Val
    610                 615                 620

Asn Asp Asn Pro Ala Gly Lys Val Leu Ala Thr Asp Tyr Gly Lys Glu
625                 630                 635                 640

Tyr Tyr Ala Ser Met Ser Phe Ala Gly Met Pro Asp Gly Arg Arg Val
                645                 650                 655

Met Leu Ala Trp Met Thr Asn Trp Asp Tyr Pro Phe Ala Phe Pro Thr
            660                 665                 670

Glu Gly Trp Lys Gly Val Leu Ser Ile Pro Arg Glu Leu Thr Leu Gln
        675                 680                 685

Lys Thr Asp Lys Gly Ile Arg Leu Ala Gln Thr Pro Ile Arg Glu Leu
    690                 695                 700

Glu Ser Leu Arg Gly Gln Leu Leu Phe Ala Ala Ser Asp Arg Arg Val
705                 710                 715                 720

Gln Ala Asp Arg Glu Asn Leu Leu Lys Gly Val Ser Gly Val Tyr
                725                 730                 735

Glu Ile Glu Ala Glu Ile Glu Ile Pro Gln Ala Ser Asn Val Ser Glu
            740                 745                 750

Phe Gly Phe Arg Leu Arg Glu Gly Ala Gly Lys Arg Thr Val Val Gly
        755                 760                 765

Tyr Lys Thr Lys Glu Asn Glu Ile Tyr Val Asp Arg Ser Leu Ser Gly
    770                 775                 780

Asp Thr Gly Phe Ser Glu Arg Phe Thr Thr Leu His Gln Ala Pro Leu
785                 790                 795                 800

Gln Pro Asp Asn Arg Arg Val Lys Leu Arg Ile Phe Val Asp Asp Ser
                805                 810                 815

Ser Leu Glu Val Phe Gly Gly Asp Gly Arg Val Val Phe Ser Glu Val
            820                 825                 830

Ile Phe Pro Asp Pro Ala His Arg Glu Met Ser Leu Phe Thr Val Gly
        835                 840                 845

Gly Glu Val Asn Val Val Ser Leu Lys Val His Ala Leu Thr Asn Val
    850                 855                 860

Trp Asn Glu Ala Ala Glu Ser Gln Thr Ser Ile Val Met Asp Thr Ser
865                 870                 875                 880

Pro Gln Gln Met Gly Leu Gly Asp Thr Arg Thr Leu Tyr Ala Ala Val
                885                 890                 895

Asn Gly Gly Ala Lys Gly Gly Arg Ser Gly Gly Ser Asp Gly Asn Arg
            900                 905                 910

Asn Gln Pro Ile Arg Arg Pro Ala Ala Lys Leu Ile Asp Cys Thr Met
        915                 920                 925

Pro Lys Thr Ile Ile Arg Lys Asp Arg Glu Thr Phe Asn Ile Leu
    930                 935                 940
```

<210> SEQ ID NO 6
<211> LENGTH: 2832
<212> TYPE: DNA
<213> ORGANISM: Paenibacillus macerans

<400> SEQUENCE: 6

| | | |
|---|---|---|
| atgggcaaag gaaaatccgt attatccatc cttttgtcct ccgcgcttat ttttgccggg | 60 |
| cttgatgctg ggatggtccg ggcggcaggc gcggagacgg aaacgggaaa gggggcaaag | 120 |

-continued

| | |
|---|---|
| gccatttttg aaagcgcaac caaattggag acgaatttga ccggctggcg aatcgaggga | 180 |
| aaaggccgaa tggagacggt ggagcagggg cttctgctcg tctcggagcc gagggagaac | 240 |
| gtgatggccc tgacgaaaac ccgggcggcc gattttatct atgaagccga cgtcatggta | 300 |
| acggagaggc aggcggacgc cacgttggta ttccgctcca atcaggatgg gtggtcctcc | 360 |
| tacatgcttc agctcgtgcc gaacgcggga ttgatccggc taaggatgc aagcgaagac | 420 |
| ggcaagctgc gggaagaacg gcgggtggac ttggccgaag gggaaatcta tcatctgaaa | 480 |
| gtcaaagccg aaggaacccg gcttcaggta ttttgggggg accgttataa accgttgatc | 540 |
| gacgtccatg acgggctta tgcttccggc tatttgggcc tgaacgtttg ggacggctcc | 600 |
| gcgctgtttc agaacgtgaa ggtcagcgaa ctgaacagca atttaggcgc ggcgatcgcg | 660 |
| agttttggag tctggcagcc ggacctgcgg ggggagctgg aacggcgga cggtaccggg | 720 |
| cgggcgctgc ggctttatca gggggctgag cgggatctcg tgctggaagg aaacgtgtct | 780 |
| tttgccgcag accaggggga agccggtttg cggttcagag cgaacgggca ggggacggac | 840 |
| ggctacgagg cggcttttgcg aaaagacggc ggccaggttt gggcggagct gagaaaagcg | 900 |
| gacggccgcg tcatcgcggc ctcggaacgt gcttacccgt cggcttccaa agcaaggcac | 960 |
| catctggaaa tccatgcgct cgggagccgg attcaggtct atgtggacgg atacgccgaa | 1020 |
| ccggccgtgg atgccgttga caatagctac gcggacggtc acgcgggatt tgcggtatcc | 1080 |
| gggggagcgg catattttca ggacgtctat ttgactgcgg ccaatgatta ttatacggaa | 1140 |
| aaataccgcc ccgactacca ttattcgccc gcccgcgggt cggcaagcga tccgaacgga | 1200 |
| ctggtctatt acgaagggga ataccatctg tttcatcagg acggcggaac ttgggcgcac | 1260 |
| gcggtcagca ccgatctcgt tcattggaag cgcttgccta tcgctttgcc ctggaacgat | 1320 |
| ttgggccatg tctggtcggg ttcggccgtc gccgatctcc ataatgcctc cggcttgttc | 1380 |
| gcggattccg ggggcaaagg cctgatcgcc tattatactt cctataatcc ggaccgcccg | 1440 |
| aacggcaacc agcgcattgg gctggcgtac agcaaggatc gcggccgcac ctggagtac | 1500 |
| gccgcagagc gcccgatcgt gatcgaaaat ccgggcaagc aggggacga tccgggagga | 1560 |
| tgggattttc gcgatcccaa ggtcgtgcgg gatgaagagc ataaccgctg ggttatggtt | 1620 |
| gtgtccggcg cgaccatat ccgcttttc acttcgacca acctgatcga ctggacgctg | 1680 |
| accgacagct tcggatacgg ggcttatgtc cgcggcggcg tgtgggagtg ccccgattta | 1740 |
| ttccaactgg ccgtggacga cacgggcgag aaaaaatggg tgctcatgat cagcacgggg | 1800 |
| gccaacccga atacgcaggg ttcggccgcg gagtatttta ttggggagct tactccggaa | 1860 |
| ggtaagttcg ttaacgacaa ccctgccggc aaggtgctgg cgaccgatta cggaaaagag | 1920 |
| tactacgcct ctatgtcttt tgccggtatg ccggacggac gcaggtgat gctggcctgg | 1980 |
| atgacgaact gggattaccc gtttgctttt ccgaccgagg gttggaaggg ggttctaagc | 2040 |
| attccgcgcg agttaacgct gcagaagacg gacaagggaa tccgcctggc acagacgccg | 2100 |
| atccgcgagc tggaatcgct gcgcggccag ctgctgtttg cggcgtcgga ccgccgcgtc | 2160 |
| caagcggata gggagaattt actgaaaggc gtgtcctcag gagtctatga aattgaagcc | 2220 |
| gaaattgaaa ttcctcaggc cagcaacgtg agcgaattcg gtttccgcct ccgcgaggga | 2280 |
| gccggaaagc ggacggtcgt cgggtacaaa acaaaagaga acgagatcta cgtggatcgc | 2340 |
| tcccttttccg cgacaccgg cttctccgag cggttcacca cgcttcatca ggcgccgctt | 2400 |
| cagccggaca accggcgtgt gaagctgcgg attttcgtga cgattcctc gctggagta | 2460 |
| ttcggagggg atggccgcgt agtattttcg gaggtgattt ttcccgatcc tgcgcaccgt | 2520 |

```
gaaatgagcc tttttactgt aggtggagag gtgaacgtgg tttccttgaa agtgcacgca    2580
ctaacaaacg tatggaacga ggcggcggag agccaaacct ccatcgtgat ggacacgagt    2640
ccgcagcaaa tggggctggg agatacccgg accttgtatg cggcggtgaa cggcggcgcc    2700
aaaggcgggc gcagcggcgg ttcggacggc aaccgaaatc agccgatccg tcgacctgca    2760
gccaagctta tcgattgcac tatgcctaaa acaattatac gaaaagatcg cgaaactttc    2820
aatatactct ga                                                        2832
```

<210> SEQ ID NO 7
<211> LENGTH: 42
<212> TYPE: DNA
<213> ORGANISM: Paenibacillus macerans

<400> SEQUENCE: 7

```
gtcgccgggg cggccgctat caattggtaa ctgtatctca gc                          42
```

<210> SEQ ID NO 8
<211> LENGTH: 64
<212> TYPE: DNA
<213> ORGANISM: Paenibacillus macerans

<400> SEQUENCE: 8

```
gtcgcccggg agctctgatc aggtaccaag cttgtcgacc tgcagaatga ggcagcaaga    60
agat                                                                  64
```

<210> SEQ ID NO 9
<211> LENGTH: 61
<212> TYPE: DNA
<213> ORGANISM: Paenibacillus macerans

<400> SEQUENCE: 9

```
gtcggcggcc gctgatcacg taccaagctt gtcgacctgc agaatgaggc agcaagaaga    60
t                                                                     61
```

<210> SEQ ID NO 10
<211> LENGTH: 35
<212> TYPE: DNA
<213> ORGANISM: Paenibacillus macerans

<400> SEQUENCE: 10

```
gtcggagctc tatcaattgg taactgtatc tcagc                                35
```

<210> SEQ ID NO 11
<211> LENGTH: 35
<212> TYPE: DNA
<213> ORGANISM: Paenibacillus macerans

<400> SEQUENCE: 11

```
aacagctgat cacgactgat cttttagctt ggcac                                35
```

<210> SEQ ID NO 12
<211> LENGTH: 37
<212> TYPE: DNA
<213> ORGANISM: Paenibacillus macerans

<400> SEQUENCE: 12

```
aactgcagcc gcggcacatc ataatgggac aaatggg                              37
```

<210> SEQ ID NO 13

-continued

```
<211> LENGTH: 35
<212> TYPE: DNA
<213> ORGANISM: Paenibacillus macerans

<400> SEQUENCE: 13
cattctgcag cagcggcggc tatggctgta cttgc                              35

<210> SEQ ID NO 14
<211> LENGTH: 35
<212> TYPE: DNA
<213> ORGANISM: Paenibacillus macerans

<400> SEQUENCE: 14
cgcggatcca gatcttacat ggagtccaag ctttc                              35

<210> SEQ ID NO 15
<211> LENGTH: 17
<212> TYPE: PRT
<213> ORGANISM: Paenibacillus macerans

<400> SEQUENCE: 15

Ala Ser Lys Ser Asn Thr Asn Leu Ile Gly Trp Gln Val Lys Gly Lys
 1               5                  10                  15

Gly
```

2,6-β-D-FRUCTAN HYDROLASE ENZYME AND PROCESSES FOR USING THE ENZYME

CROSS-REFERENCE TO RELATED APPLICATIONS

This application is a divisional of U.S. patent application Ser. No. 09/397,885, filed on Sep. 17, 1999 (now U.S. Pat. No. 6,323,007) and claims priority under 35 U.S.C. 119 of U.S. provisional patent application No. 60/101,615, filed on Sep. 24, 1998, and No. 60/111,657, filed on Dec. 10, 1998, and Danish applications nos. PA 1998 01173, filed on Sep. 18, 1998, and PA 1998 01623, filed on Dec. 10, 1998, the contents of which are fully incorporated herein by reference.

TECHNICAL FIELD

The present invention relates to isolated polypeptides having 2,6-β-D-fructan hydrolase activity and isolated nucleic acid sequences encoding the polypeptides. The invention also relates to nucleic acid constructs, vectors, and host cells comprising the nucleic acid sequences as well as methods for producing and using the polypeptides as well as compositions comprising the polypeptides and the use thereof.

BACKGROUND ART 2,6-β-D-fructans, such as levans of bacterial origin and phleins of plant origin, are substantially β-2,6-fructose polysaccharides consisting of a variable number of fructose units combined by β-(2→6)-glycosidic linkages.

In phlein, β-2,1 branching points also exist depending on the plant origin. Many plants, in particular grasses, store phlein as reserve polysaccharides in stems and leafs. As grasses are ubiquitous plants, phlein is an attractive resource as it is available in almost unlimited amounts.

Levans originate from bacteria. In nutrient limited ecosystems, bacteria have a marked tendency to adhere to surfaces and initiate the formation of a biofilm. A biofilm is a community of microbes, embedded in an organic polymer matrix, adhering to a surface. In natural and industrial ecosystems, especially in nutrient limited systems, biofilms will predominate and cause problems as increased frictional resistance to fluids in water conduits and on ship hulls (fouling), decreased heat transfer from heat exchangers, corrosion of metallic substrates and contamination in the food and biotechnology industry. Biofilms are also a severe problem in medical science and industry causing dental plaque, contaminated endoscopes and contact lenses, prosthetic device colonization and biofilm formation on medical implants.

A biofilm is a collection of microcolonies, typically with water channels in between, and an assortment of cells and extracellular polymers (polysaccharides, glycoproteins, proteins). Bacterial extracellular polysaccharides are composed of homo- and heteropolysaccharides of particularly glucose, fucose, mannose, galactose, fructose, pyruvate, mannuronic acid or glucuronic acid based complexes. The different bonds between the saccharides give rise to a multitude of different polysaccharides including levans, polymannans, dextrans, cellulose, amylopectin, glycogen and alginate.

Bacteria growing in biofilms are more resistant to antibiotics and disinfectants than planktonic cells and the resistance increases with the age of the biofilm. Bacterial biofilm also exhibits increased physical resistance towards desiccation, extreme temperatures or light. As mentioned, biofilm formation causes industrial, environmental and medical problems and the difficulties in cleaning and disinfection of bacterial biofilm with chemicals is a major concern in many industries. Furthermore, the trend towards milder disinfection and cleaning compositions may increase the insufficient cleaning of surfaces covered with biofilm.

Levansases are known e.g. from Fuchs et al. [Fuchs A, DeBruijn J M and Niedeveld C J; Antonie van Leeuwenhoek, 1985 52 (3) 333–343].

Levanases from bacteria have been reported such as from Arthrobacter species strain 7 by Zelikson R. and Hestrin S., Biochemical Journal (1961), 79 page 71–79, from *S. salivarius* by Takahishi N, Mizuno F, Takamori K (1983) Infection and Immunicity vol 42, pp 231–236 and from *A. viscosus* by Igarashi T., Takahashi M., Yamamoto A., Etoh Y., Takamori K., (1987), Infection and immunity, Vol 55, pp. 3001–3005.

A levanase from Bacillus sp. No. L7 was reported by Miasnikov A. N. (Characterization of a novel endo levanase and its gene from bacillus sp. L7; FEMS Microbiology Letters, 1997, vol. 154, pp. 23–28).

An application of a Bacillus sp. No. 7 endo-levanase is described in WO 99/31020.

A levanase from *Bacillus polymyxa* was reported by Bezzate et al. in J. Bacteriol. (1994), 176(8), 2177–83.

U.S. Pat. No. 3,773,623 describes a composition for treating slime in industrial waters with dead cells of the yeast Rhodotorula sp. having levan hydrolase activity WO 97/01669 describes a method to remove water binders such as slime on a press felt by spraying enzymes onto or into the press felt.

EP 129315 A1 describes a separately packed two component biocidal system.

A process for the manufacture of fructose is described in JP 52136929 A and JP 52136928. A.

U.S. Pat. No. 4,927,757 describes the manufacture of fructose by use of a fructosyl transferase and a levanase.

KR 9301882 B describes the manufacture of a fructo-oligosaccharide preparation by treating a sucrose containing medium with a levanase.

SUMMARY OF THE INVENTION

The present invention relates to an isolated polypeptide having 2,6-β-D-fructan hydrolases activity, selected from the group consisting of:

(a) a polypeptide having an amino acid sequence which has at least 55.3% identity with amino acids 32 to 923 for the mature polypeptide of SEQ ID NO:1 or 25 to 1277 for the mature polypeptide of SEQ ID No. 3 or 29 to 943 for the mature polypeptide of SEQ ID No. 5;

(b) a polypeptide which is encoded by a nucleic acid sequence which hybridizes under low stringency conditions with (i) nucleotides 94 to 2769 of SEQ ID NO:2 or 73 to 3824 of SEQ ID No:4 or 85 to 2832 of SEQ ID No:6, (ii) the cDNA sequence comprised in nucleotides 94 to 2769 of SEQ ID NO:2 or 73 to 3824 of SEQ ID No:4 or 85 to 2832 of SEQ ID No:6, (iii) a subsequence of (i) or (ii) of at least 100 nucleotides, or (iv) a complementary strand of (i), (ii), or (iii);

(c) a variant of the polypeptide having an amino acid sequence of SEQ ID NO:1 or SEQ ID No. 3 or SEQ ID No. 5 comprising a substitution, deletion, and/or insertion of one or more amino acids;

(d) an allelic variant of (a) or (b);
(e) a fragment of (a), (b), or (d) that has 2,6-β-D-fructan hydrolases activity; and
(f) a polypeptide having
   i) a 2,6-β-D-fructan hydrolase activity optimum in the pH range of 3.5–91.5, measured at 37° C.;
   ii) a molecular mass greater or equal to about 88 kDa;
   iii) a 2,6-β-D-fructan hydrolase activity optimum in the temperature range of 20–70° C.

The present invention also relates to isolated nucleic acid sequences encoding the polypeptides and to nucleic acid constructs, vectors, and host cells comprising the nucleic acid sequences as well as methods for producing and using the polypeptides. Also the invention relates to a process for removing a microbial biofilm on a surface comprising contacting said biofilm with an endo-2,6-β-D-fructan hydrolase in an aqueous medium.

DETAILED DISCLOSURE OF THE INVENTION

Figure 1:
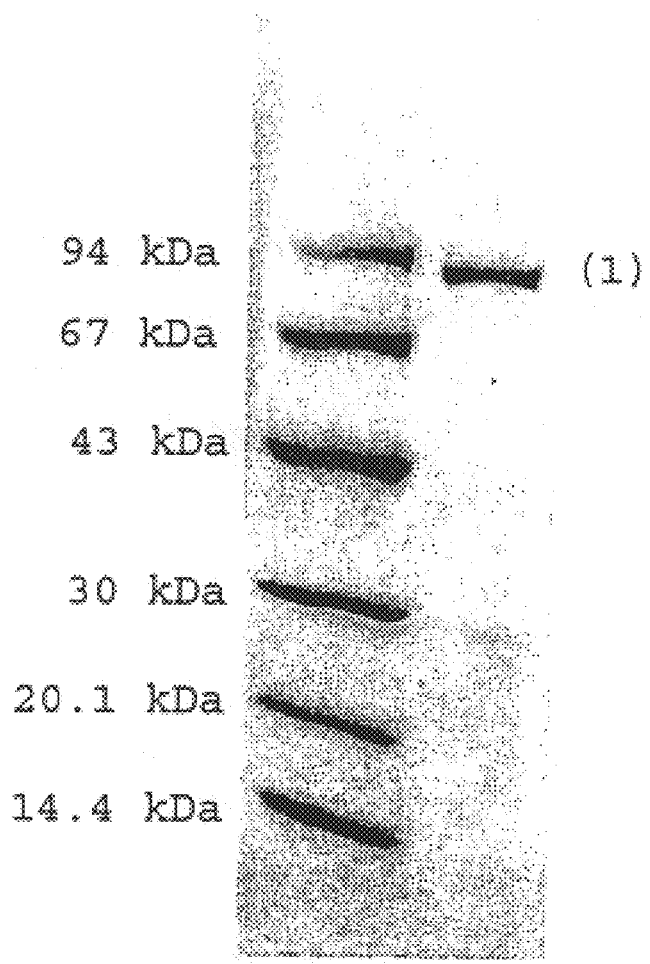
FIG. 1 shows a measurement of the molecular weight of the 2,6-β-D-fructan hydrolase of the mature part of SEQ ID No:1 compared to a series of standards as a result of SDS-PAGE analysis.

The present invention provides novel enzymes, which hydrolyzes 2,6-β-D-fructo-furanosidic linkages in 2,6-β-D-fructans (levans or phleins). Accordingly the enzymes may be classified as a 2,6-β-D-fructan hydrolase or a levanase or a phleinase or a fructan β-fructosidase.

DEFINITIONS

The term, "an isolated polypeptide" or "isolated 2,6-β-D-fructan hydrolase" as used herein about the enzyme of the invention, is a 2,6-β-D-fructan hydrolase or 2,6-β-D-fructan hydrolase part, which is at least about 20% pure, preferably at least about 40% pure, more preferably about 60% pure, even more preferably about 80% pure, most preferably about 90% pure, and even most preferably about 95% pure, as determined by SDS-PAGE.

The term "isolated polypeptide" may alternatively be termed "purified polypeptide".

The term "2,6-β-D-fructan hydrolase encoding part" as used herein in connection with a DNA sequence means the region of the DNA sequence which corresponds to the region which is translated into a polypeptide sequence. The translated polypeptide may comprise, in addition to the mature sequence exhibiting 2,6-β-D-fructan hydrolase activity, an N-terminal signal sequence. The signal sequence generally guides the secretion of the polypeptide. For further information see (Stryer, L., "Biochemistry" W. H., Freeman and Company/New York, ISBN 0-7167-1920-7). In the present context the term "2,6-β-D-fructan hydrolase encoding part" is intended to cover the translated polypeptide and the mature part thereof.

The term 2,6-β-D-fructan hydrolase as used herein is defined according to the Enzyme classification (EC), as having the EC-number: EC 3.2.1.65 in accordance with *Recommendations* (1992) *of the Nomenclature Committee of the International Union of Biochemistry and Molecular Biology,* Academic Press, Inc., 1992. The term 2,6-β-D-fructan hydrolase alternatively be termed levanase.

The term "surface" as used herein relates to any surface which is essentially non-permeable to microorganisms. Examples of surfaces are surfaces made from metal, e.g. stainless steel alloys, plastics/synthetic polymers, rubber, board, glass, wood, paper, textile, concrete, rock, marble, gypsum and ceramic materials which optionally may be coated, e.g. with paint, enamel, polymers and the like. The surface may however also be of biological origin such as mucous membranes, skin, teeth, hair, nails etc.

2,6-β-D-fructan hydrolases activity as used herein is defined as the ability of an enzyme of hydrolyzing 2,6-β-D-fructo-furanosidic linkages in 2,6-β-D-fructans. A measure of 2,6-β-D-fructan hydrolases activity is a Levan Reducing sugar Unit (LRU), where 1 LRU is defined as the amount of enzyme that generates an amount of reducing groups in a levan substrate equivalent to 1 μmol fructose per minute. The conditions for measuring 2,6-β-D-fructan hydrolases activity is given in the "Materials and methods" section, infra.

The 2,6-β-D-fructan hydrolase

The isolated polypeptide provided by the invention is a polypeptide obtained from a strain of Paenibacillus exhibiting 2,6-β-D-fructan hydrolase activity.

Properties

In a preferred embodiment the isolated polypeptide is further characterized by having one or more of the following properties:
   a) a 2,6-β-D-fructan hydrolase activity optimum in the pH range of 3.5–9.5, measured at 37° C.;
   b) a molecular mass greater or equal to about 88 kDa;
   c) a 2,6-β-D-fructan hydrolase activity optimum in the temperature range of 20–70° C.;

A preferred pH-activity optimum range is from about 3.5 to about 8.5. A more preferred pH-activity optimum range is from about 5.5 to about 7.5, while a most preferred range is from about 6.5 to about 6.75 measured at in the 2,6-β-D-fructan hydrolase assay at 37° C. as described vide infra.

Polypeptides of the invention is surprisingly quite large. Accordingly the molecular weight of a polypeptide of the invention greater or equal to about 88 as determined by SDS-PAGE gel electrophoresis as described in Sambrook et al.; *Molecular Cloning: A Laboratory Manual;* 1989,; Cold Spring Harbor Lab.; Cold Spring Harbor; N.Y.

A preferred temperature-activity optimum range is from about 25° C. to about 55° C., while a most preferred temperature-activity optimum range is from about 35° C. to about 40° C., e.g. about 37° C., measured at in the 2,6-β-D-fructan hydrolase assay at pH 6.5 as described vide infra.

Preferred substrates for a polypeptide having 2,6-β-D-fructan hydrolase activity of the invention are compounds comprising 2,6-fructose furanosidic bonds, such as levans and phleins specifically, in which, the 2,6-β-D-fructan hydrolases cleave β-2,6-fructose furanosidic bonds.

The polypeptides of the present invention have at least 20%, preferably at least 40%, more preferably at least 60%, even more preferably at least 80%, even more preferably at least 90%, and most preferably at least, 100% of the 2,6-β-D-fructan hydrolase activity of the mature polypeptide of SEQ ID No:1 or SEQ ID No:3 or SEQ ID No:5.

Structure

In further preferred embodiments, the isolated polypeptide is selected from one of the following groups:

a) An isolated polypeptide encoded by the nucleotide sequence inserted into plasmid pSJ1678 present in *E. coli* DSM 12406 or the nucleotide sequence inserted into plasmid pSJ1678 present in *E. coli* DSM 13028 or the nucleotide sequence inserted into plasmid pSJ1678 present in *E. coli* DSM 13029.

b) An isolated polypeptide having 2,6-β-D-fructan hydrolase activity which is encoded by a nucleic acid sequence which hybridize under medium stringency conditions, preferably medium-high stringency conditions, more preferably high stringency conditions, and most preferably very high stringency conditions with a nucleic acid probe which hybridizes under the same conditions with (i) nucleotides 94 to 2769 of SEQ ID NO:2 or 73 to 3824 of SEQ ID No:4 or 85 to 2832 of SEQ ID No:6, (ii) the cDNA sequence comprised or contained in these nucleotide sequences, (iii) a subsequence of (i) or (ii), or (iv) a complementary strand of (i), (ii), or (iii) (J. Sambrook, E. F. Fritsch, and T. Maniatus, 1989, Molecular Cloning, A Laboratory Manual, 2d edition, Cold Spring Harbor, N.Y.). The subsequence of SEQ ID No:2 or SEQ ID No:4 or SEQ ID No:6 may be at least 100 nucleotides or preferably at least 200 nucleotides. Moreover, the subsequence may encode a polypeptide fragment which has 2,6-β-D-fructan hydrolase activity. The polypeptides may also be allelic variants or fragments of the polypeptides that have 2,6-β-D-fructan hydrolase activity.

c) An isolated polypeptide having 2,6-β-D-fructan hydrolase activity and having an amino acid sequence which has a degree of identity to amino acids 32 to 923 of SEQ ID NO: 1, 25 to 1277 or SEQ ID No. 3 or 29 to 943 of SEQ ID No. 5 (herein after "mature polypeptide") of at least 55.3%, preferably at least about 65%, more preferably about at least 70%, even more preferably about at least 80%, even more preferably about at least 90%, even more preferably about at least 95% and most preferably about at least 97% (herein after "homologous polypeptides"). Preferred homologous polypeptides have an amino acid sequence which differs by five amino acids, preferably by four amino acids, more preferably by three amino acids, even more preferably by two amino acids, and most preferably by one amino acid from amino acids of said sequences.

d) A polypeptide comprising the amino acid sequence of SEQ ID No. 1, 3 or 5 having 2,6-β-D-fructan hydrolase activity, preferably comprising the amino acid sequence of the mature polypeptide.

e) An isolated polypeptide comprising an allelic variant of the amino acid sequence of SEQ ID No. 1 or 3 or 5 having 2,6-β-D-fructan hydrolase activity, preferably comprising the amino acid sequence of an allelic variant of the mature polypeptide.

f) An isolated polypeptide consisting of the amino acid sequence of SEQ ID No. 1, 3 or 5, preferably consisting of the amino acid sequence of the mature polypeptide.

g) An isolated polypeptide consisting of an allelic variant of the amino acid sequence of SEQ ID No. 1, 3 or 5, preferably consisting of the amino acid sequence of an allelic variant of the mature polypeptide.

h) A fragment of the polypeptide of SEQ ID No:1 or SEQ ID No. 3 or SEQ ID No. 5 or the mature polypeptides thereof having 2,6-β-D-fructan hydrolase activity.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

A fragment of a polypeptide of SEQ ID No:1 or SEQ ID No. 3 or SEQ ID No. 5 or the mature polypeptides thereof having 2,6-β-D-fructan hydrolase activity is a polypeptide having one or more amino acids deleted from the amino and/or carboxyl terminus of this amino acid sequence. It is presently contemplated that the first approximately 400 amino acids in the N-terminal of mature polypeptides having 2,6-β-D-fructan hydrolase activity from Paenibacillus strains constitutes one or more putative levan binding domains. It is also contemplated that for some of these polypeptides, e.g. from *Paenibacillus pabuli,* an additional putative levan binding domain are present in the C-terminal of the polypeptide. Accordingly 2,6-β-D-fructan hydrolases of the invention mat comprise one or more levan binding domains.

The amino acids in position 1–31 in SEQ ID No:1, 1–24 in SEQ ID No:3 and 1–28 in SEQ ID No:5 are predicted to be signal peptides, whereas the amino acids in position 32 to 923, 25 to 1277 and 29 to 943 are predicted to be the mature 2,6-β-D-fructan hydrolase. The prediction was made by using the SignalP neural network computer program described by Nielsen H., Engelbrecht J., Brunak S., von Heijne G.; *Identification of prokaryotic and eukaryotic signal peptides and prediction of their cleavage sites;* Protein Engineering; 1997; vol. 10, pp. 1–6. However, surprisingly when the polypetide of SEQ ID No:1 was purified from a strain of *Bacillus subtilis* the N-terminal sequence was found to be different than the one predicted using SignalP neural network computer program. Accordingly a most preferred polypeptide or an allelic variant or a fracment thereof has the sequence of amino acids 54 to 923 of SEQ ID No:1 (see examples).

For purposes of the present invention, the degree of homology (identity) between two protein sequences is determined by the Clustal method (Thompson, J. D., Higgins, D. G., and Gibson, T. J., (1994), Nucleic Acids research 22, 4673–4680) with an PAM250 residue table, and the default settings of the Megalign program in the Lasergene package (DNAstart Inc., 1228 South Park Street, Madison, Wis. 53715). The settings for multiple alignment are; gap penalty of 10, and a gap length penalty of 10 while the pairwise alignment parameters are gap penalty of 3, Ktuple of 1, windows=5 and diagonals=5.

In an additional preferred embodiment the polypeptide is a variant of the polypeptide having an amino acid sequence of SEQ ID No:1 or SEQ ID No:3 or SEQ ID No:5 comprising a substitution, deletion, and/or insertion of one or more amino acids.

The amino acid sequences of the variant polypeptide may differ from the amino acid sequence of SEQ ID No:1 or SEQ ID No:3 or SEQ ID No:5 or the mature polypeptides thereof by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

As defined herein, an "isolated" polypeptide is a polypeptide which is essentially free of other non-[enzyme] polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Nucleic Acid Sequences

The invention also relates to isolated nucleic acid sequences which encode a polypeptides of the present invention. The isolated nucleic acid sequence is preferably selected from one of the following groups:

a) The 2,6-β-D-fructan hydrolase polypeptide encoding parts of the nucleic acid sequences contained in plasmids pSJ1678 that are contained in *E. coli* strain DSM 12406 or *E. coli* strain DSM 13029 or *E. coli* strain DSM 13028.

b) The mature 2,6-β-D-fructan hydrolase polypeptide encoding parts of the nucleic acid sequences contained in plasmids pSJ1678 that are contained in *E. coli* strain DSM 12406 or *E. coli* strain DSM 13029 or *E. coli* strain DSM 13028.

c) The nucleic acid sequence shown in SEQ ID No:2 or SEQ ID No:4 or SEQ ID No:6 or more preferred the sequence of SEQ ID NO: 2 or SEQ ID No:4 or SEQ ID No:6 encoding the mature 2,6-β-D-fructan hydrolase polypeptides.

d) An isolated nucleic acid sequence which encode a 2,6-β-D-fructan hydrolase polypeptide having the amino acid sequence of SEQ ID NO:1 or SEQ ID No:3 or SEQ ID No:5 or the mature polypeptides thereof, which differ from SEQ ID NO:1 or SEQ ID No:4 or SEQ ID No:6 by virtue of the degeneracy of the genetic code.

e) An isolated subsequence of SEQ ID No:2 or SEQ ID No:4 or SEQ ID No:6 which encode fragments of SEQ ID NO:1 or SEQ ID No:3 or SEQ ID No:5 that have 2,6-β-D-fructan hydrolase activity. A subsequence of No:2 or SEQ ID No:4 or SEQ ID No:6 is a nucleic acid sequence encompassed by No:2 or SEQ ID No:4 or SEQ ID No:6 except that one or more nucleotides from the 5' and/or 3' end have been deleted. Preferably, a subsequence contains at least 2100 nucleotides, more preferably at least 1800 nucleotides, and most preferably at least 1500 nucleotides.

f) An isolated mutant nucleic acid sequence comprising at least one mutation in the mature polypeptide coding sequence of No:2 or SEQ ID No:4 or SEQ ID No:6, in which the mutant nucleic acid sequence encodes a polypeptide which consists of amino acids 32–923 of SEQ ID NO:1 or 25 to 1277 of SEQ ID No:3 or 29 to 943 of SEQ ID No:5.

g) An isolated nucleic acid sequence which have a degree of homology to the mature polypeptide coding sequence of SEQ ID No:2 or SEQ ID No:4 or SEQ ID No:6 (i.e., nucleotides 94 to 2769 or 73 to 3824 or 85 to 2832) of at least about 56%, preferably about 65%, more preferably about 70%, more preferably about 80%, more preferably about 90%, even more preferably about 95%, and most preferably about 97% homology, which encode an active polypeptide.

h) An isolated nucleic acid sequence encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with the nucleic acid sequence of SEQ ID No:2 or SEQ ID No:4 or SEQ:ID No:6 or their complementary strands; or allelic variants and subsequences thereof (Sambrook et al., 1989, supra), as defined herein.

i) An isolated nucleic acid sequences produced by (a) hybridizing a DNA under very low, low, medium, medium-high, high, or very high stringency conditions with (i) nucleotides 94 to 2769 of SEQ ID No:2 or 73 to 3824 of SEQ ID No:4 or 85 to 2832 of SEQ ID No:6, (ii) the cDNA sequence comprised or contained in nucleotides 94 to 2769 of SEQ ID No:2 or 73 to 3824 of SEQ ID No:4 or 85 to 2832 of SEQ ID No:6, (iii) a subsequence of (i) or (ii), or (iv) a complementary strand of (i), (ii), or (iii); and (b) isolating the nucleic acid sequence. The subsequence is preferably a sequence of at least 100 nucleotides such as a sequence which encodes a polypeptide fragment which has 2,6-β-D-fructan hydrolase activity.

The techniques used, to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Paenibacillus, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

For purposes of the present invention, the degree of homology (identity) between two nucleic acid sequences is determined by the Clustal, method (Thompson, J. D., Higgins, D. G., and Gibson, T. J., (1994), Nucleic Acids research 22, 4673–4680) with an PAM250 residue table, and the default settings of the Megalign program in the Lasergene package (DNAstart Inc., 1228 South Park Street, Madison, Wis. 53715). The settings for multiple alignment are; gap penalty of 10, and a gap length penalty of 10 while the pairwise alignment parameters are gap penalty of 5 and Ktuple of 2, windows=4 and diagonals=4.

The nucleic acids in position 1–93 in SEQ ID No:2, 1–72 in SEQ ID No:4 and 1–84 in SEQ ID No:6 are predicted to encode signal peptides, whereas the nucleic acids in position 94 to 2769 of SEQ ID No:2, 73 to 3824 of SEQ ID No:4 and 85 to 2832 of SEQ ID No:6 are predicted to encode mature 2,6-β-D-fructan hydrolases. The prediction was made by using the SignalP neural network computer program described by Nielsen H., Engelbrecht J., Brunak S., von Heijne G.; *Identification of prokaryotic and eukaryotic signal peptides and prediction of their cleavage sites;* Protein Engineering; 1997; vol. 10, pp. 1–6.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ, in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID No:2 or SEQ ID No:4 or SEQ ID No:6, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, Protein Expression and Purification 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, Science 244: 1081–1085). In the latter technique, mutations are introduced at every positively charged residue in the molecule, and the resultant mutant molecules are tested for 2,6-β-D-fructan hydrolase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, Science 255: 306–312; Smith et al., 1992, Journal of Molecular Biology 224: 899–904; Wlodaver et al., 1992, FEBS Letters 309: 59–64).

The nucleic acid sequences of SEQ ID No:2 or SEQ ID No:4 or SEQ ID No:6 or a subsequence thereof, as well as the amino acid sequences of SEQ ID No:1 or SEQ ID No:3 or SEQ ID No:5 or a fragment thereof, may be used to design a nucleic acid probe to identify and clone DNA encoding polypeptides having 2,6-β-D-fructan hydrolase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

Thus, a genomic DNA or cDNA library prepared from such other organisms may be screened for DNA which hybridizes with the probes described above and which encodes a polypeptide having 2,6-β-D-fructan hydrolase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID No:2 or SEQ ID No:4 or SEQ ID No:6 or a subsequence thereof, the carrier material is used in a Southern blot. For purposes of the present invention, hybridization indicates that the nucleic acid sequence hybridizes to a labeled nucleic acid probe corresponding to the nucleic acid sequences shown in SEQ ID No:2 or SEQ ID No:4 or SEQ ID No:6, their complementary strands, or a subsequence thereof, under very low to very high stringency conditions. Molecules to which the nucleic acid probe hybridizes under these conditions are detected using X-ray film.

In a preferred embodiment, the nucleic acid probe is a nucleic acid sequence which encodes the polypeptide of SEQ ID No:1 or SEQ ID No:3 or SEQ ID No:5, or a subsequence thereof. In another preferred embodiment, the nucleic acid probe is SEQ ID No:2 or SEQ ID No:4 or SEQ ID No:6. In another preferred embodiment, the nucleic acid probe is the mature polypeptide coding region of SEQ ID No:2 or SEQ ID No:4 or SEQ ID No:6. In another preferred embodiment, the nucleic acid probe is the nucleic acid sequence contained in plasmid pSJ1678 which is contained in E. coli strain DSM 12406 or E. coli strain DSM 13029 or E. coli strain DSM 13028, wherein the nucleic acid sequence encodes a polypeptide having 2,6-β-D-fructan hydrolase activity. In another preferred embodiment, the nucleic acid probe is the mature polypeptide coding region contained in plasmid pSJ1678 which is contained in E. coli strain DSM 12406 or E. coli strain DSM 13029 or E. coli strain DSM 13028.

For long probes of at least 100 nucleotides in length, very low to very high stringency conditions are defined as pre-hybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at 50° C. to 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast, RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Microbial Sources

A polypeptide of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted. In a preferred embodiment, the polypeptide is secreted extracellularly.

The 2,6-β-D-fructan hydrolase as shown in SEQ ID No:1 or SEQ ID No:3 or SEQ ID No: 5 are obtained from strains of Paenibacillus. More specifically the 2,6-β-D-fructan hydrolase producing strains are Paenibacillus amylolyticus, Peanibacillus pabuli or Peanibacillus macerans. Samples of these microorganisms was deposited by the applicant according to the Budapest Treaty on the International Recognition of the Deposits of Microorganisms for the Purpose of Patent Procedures at Deutsche Sammlung von Mikroorganismen und Zellkulturen GmbH, under under Accession No. DSM 12458 for the Paenibacillus amylolyticus, accession No. DSM 13026 for Paenibacillus pabuli and accession No. DSM 13025 for Paenibacillus macerans. These strains were acquired from commercially available strain collections.

These deposited examples of isolated substantially pure biological cultures of Paenibacillus (any mutant of said Paenibacillus strains having retained the 2,6-β-D-fructan hydrolase encoding capability is considered to be included in the present invention), was used to obtain the DNA sequences encoding 2,6-β-D-fructan hydrolases of the invention.

In accordance with Jones D. and Collins M. D.; Bergey's manual of Systematic Bacteriology; Sneath P. H. A., Mair N. S., Sharpe M. E., Holt J. G. (Eds.); Williams & Wilkins; Baltimore/London; 1986, Vol.2, p. 1105–1139, the microorganisms of the invention are aerobic endospore forming bacterias belonging to the genus Paenibacillus. The optimum temperature for growth is about 30–40° C. The microorganism is a common gram positive soil bacteria.

Methods for Producing Mutant Nucleic Acid Sequences

The present invention further relates to methods for producing a mutant nucleic acid sequence, comprising introducing at least one mutation into the mature polypeptide coding sequence of SEQ ID No:2 or SEQ ID No:4 or SEQ ID No:6 or a subsequence thereof, wherein the mutant nucleic acid sequence encodes a polypeptide which consists of amino acids 32 to 923 of SEQ ID No:1 or 25 to 1277 of SEQ ID No:3 or 29 to 943 of SEQ ID No:5 or a fragment thereof which has 2,6-β-D-fructan hydrolase activity.

The introduction of a mutation into the nucleic acid sequence to exchange one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of the present invention. The term "coding sequence" is defined herein as a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penp), *Bacillus subtilis* xylA and xylB genes, and prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for Bacillus NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109–137.

In a preferred embodiment, the signal peptide coding region is nucleotides 1 to 95 of SEQ ID No:2 or 1 to 72 of SEQ ID No:4 or 1 to 84 of SEQ ID No:6 which encode amino acids 1 to 31 of SEQ ID NO:1 or 1 to 24 of SEQ ID No:3 or 1 to 28 of SEQ ID No:5.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an, autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from Bacillus subtilis or Bacillus licheniformis, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG, (orotidine-5′-phosphate decarboxylase), sC (sulfate adenyltransferase), trpC (anthranilate synthase), as well as equivalents thereof. Preferred for use in an Aspergillus cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli,* and pUB110, pE194, pTA1060, and pAMβ1 permitting replication in Bacillus. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a Streptomyces cell, e.g., *Streptomyces lividans* or *Streptomyces murinus*, or gram negative bacteria such as *E. coli* and Pseudomonas sp. In a preferred embodiment, the bacterial host cell is a *Bacillus lentus, Bacillus licheniformis, Bacillus stearothermophilus*, or *Bacillus subtilis* cell. In another preferred embodiment, the Bacillus cell is an alkalophilic Bacillus.

The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred embodiment, the yeast host cell is a Candida, Hansenula, Kluyveromyces, Pichia, Saccharomyces, Schizosaccharomryces, or Yarrowia cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thalilus and carbon catabolism may be fermentative.

In an even more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, or Trichoderma.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host: cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In an even most preferred embodiment, the filamentous fungal parent cell is a *Fusarium venenatum (Nirenberg* sp. *nov.)* cell. In another most preferred-embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. Suitable methods for transforming Fusarium species are described by Malardier et al., 1989, *Gene* 78: 147–156 and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a strain, which in its wild-type form is capable of producing the polypeptide, to produce a supernatant comprising the polypeptide; and (b) recovering the polypeptide. Preferably, the strain is of the genus Paenibacillus, and more preferably *Paenibacillus amylolyticus* or *Paenibacillus pabuli* or *Paenibacillus macerans*.

The present invention also relates to methods for producing a polypeptide of the present invention comprising (a) cultivating a host cell under conditions conducive for production of the polypeptide; and (b) recovering the polypeptide.

The present invention also relates to methods for producing a polypeptide of the present invention comprising (a)

cultivating a host cell under conditions conducive for production of the polypeptide, wherein the host cell comprises a mutant nucleic acid sequence having at least one mutation in the mature polypeptide coding region of SEQ ID No:2 or SEQ ID No:4 or SEQ ID No:6, wherein the mutant nucleic acid sequence encodes a polypeptide which consists of amino acids 32 to 923 of SEQ ID No:1 or 25 to 1277 of SEQ ID No:3 or 29 to 943 of SEQ ID No:5, and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial, suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Plants

The present invention also relates to a transgenic plant, plant part, or plant cell which has been transformed with a nucleic acid sequence encoding a polypeptide having 2,6-β-D-fructan hydrolase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as festuca, lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present inventions may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285–294). Organ-specific promoters may be, for example, a promoter from storage sink tissues such as seeds, potato tubers, and fruits (Edwards & Coruzzi, 1990, *Ann. Rev. Genet.* 24: 275–303), or from metabolic sink tissues such as meristems (Ito et al., 1994, *Plant Mol. Biol.* 24: 863–878), a seed specific promoter such as the glutelin, prolamin, globulin, or albumin promoter from rice (Wu et al., 1998, *Plant and Cell Physiology* 39: 885–889), a *Vicia faba* promoter from the legumin B4 and the unknown seed protein gene from *Vicia faba* (Conrad et al., 1998, *Journal of Plant Physiology* 152: 708–711), a promoter from a seed oil body protein (Chen et al., 1998, Plant and Cell Physiology 39: 935–941), the storage protein napA promoter from *Brassica napus,* or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991–1000, the chlorella virus adenine methyltransferase gene promoter (Mitra and Higgins, 1994, *Plant Molecular Biology* 26: 85–93), or the aldP gene promoter from rice (Kagaya et al., 1995, *Molecular and General Genetics* 248: 668–674), or a wound inducible promoter such as the potato pin2 promoter (Xu et al., 1993, *Plant Molecular Biology* 22: 573–588).

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including Agrobacterium-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15–38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275–281; Shimamoto, 1994, *Current Opinion Biotechnology* 5: 158–162; Vasil et al., 1992, *Bio/Technology* 10: 667–674). An alternative method for transformation of monocots is based on protoplast transformation as described by Omirulleh et al., 1993, *Plant Molecular Biology* 21: 415–428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or as plant cell comprising a nucleic acid sequence encoding a polypeptide having 2,6-β-D-fructan hydrolase activity of the present invention under conditions conducive for production of the polypeptide; and (b) recovering the polypeptide.

Compositions

In a still further aspect, the present invention relates to compositions comprising a polypeptide of the present invention. Preferably, the compositions are enriched in a polypeptide of the present invention. In the present context, the term "enriched" indicates that the 2,6-β-D-fructan hydrolase activity of the composition has been increased, e.g., with an enrichment factor of 1.1.

The composition may comprise a polypeptide of the invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be producible by means of a microorganism belonging to the genus Aspergillus, preferably, *Aspergillus aculeatus, Aspergillus awamori, Aspergillus niger,* or *Aspergillus oryzae,* or Trichoderma, Humicola, preferably *Humicola insolens,* or Fusarium, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum.*

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Applications

The 2,6-β-D-fructan hydrolases of the invention may be applied in various processes. Said 2,6-β-D-fructan hydrolases may be as described vide supra be comprised in a liquid or solid composition, which ever is suitable for the intended application.

Disintegration/removal of Biofilm

One preferred process is disintegration and/or removal of biofilm. The term "disintegration" as used herein is to be understood as hydrolysis of polysaccharides in a biofilm matrix connecting and binding together individual microbial cells in the biofilm whereby the microbial cells can be released and removed from the biofilm. The biofilm is preferably present at a surface and the disintegration of the biofilm is preferably achieved by bringing the surface in contact, e.g. by immersing, covering or splashing the surface with an aqueous medium comprising a 2,6-β-D-fructan hydrolase, thus disintegrating and removing the biofilm from the surface whereon to it is attached. It is presently contemplated that the 2,6-β-D-fructan hydrolase of the invention is an endo-2,6-β-D-fructan hydrolase, which surprisingly may be produced in quantities sufficient to test on biofilm matrices. Accordingly the invention relates to a process for disintegrating a microbial biofilm on a surface comprising contacting said biofilm with an endo-2,6-β-D-fructan hydrolase in an aqueous medium as well as a process for disintegrating a microbial biofilm comprising contacting said biofilm with a 2,6-β-D-fructan hydrolase of the invention. A 2,6-β-D-fructan hydrolase of the invention may also be used to hydrolyse slime e.g. in white waters in the pulping and paper industry. As opposed to a biofilm as defined, supra, slime is solubilized polysaccharides, which increases the viscosity of the aqueous medium in which it is dissolved.

The 2,6-β-D-fructan hydrolase may be present in the aqueous medium in amounts of 0.0001 to 10000 mg/l, preferably 0.001–1000 mg/l more preferably 0.01–100 mg/l, most preferably 0.1–10 mg/l.

The process may suitably be performed at temperatures from about ambient temperature to about 70° C. A more preferred temperature range is from about 30° C. to about 60° C., e.g. about 40° C. to about 50° C.

A suitable pH for the process lies within from about 3.5 to about 8.5. A more preferred pH range is from about 5.5 to about 8, e.g. from about 6.5 to about 7.5. The contact time or reaction time for the 2,6-β-D-fructan hydrolase to effectively removing a biofilm may vary considerably, depending on the biofilm properties and the frequency of which a surface is treated with the 2,6-β-D-fructan hydrolase, but preferably a suitable reaction time lies within 0.25–25 hours, more preferred 1–10 hours, e.g. 2 hours.

A biofilm may also suitably be removed by contacting the biofilm with the 2,6-β-D fructan hydrolases of the invention in combination with one or more other enzymes and/or active compounds. Thus the 2,6-β-D-fructan hydrolases may be combined with on or more suitable hydrolases such as cellulases, hemicellulases, xylanases, amylases, lipases, proteases and/or pectinases. The 2,6-β-D-fructan hydrolases of the invention may further be combined with antimicrobial agents such as enzymatic or non-enzymatic biocides. An enzymatic biocide may e.g. be a composition comprising an oxidoreductase, e.g. a laccase or a peroxidase, especially haloperoxidase, and optionally an enhancing agent such as an alkyl syringate as described in patent applications WO97/42825 and DK97/1273 (not published at the filing date).

The surface from which a biofilm is to be removed and/or cleaned off is in one preferred embodiment a hard surface, which by definition relates to any surface which is essentially non-permeable to microorganisms. Examples of surfaces are surfaces made from metal, e.g. stainless steel alloys, plastics/synthetic polymers, rubber, board, glass, wood, paper, textile, concrete, rock, marble, gypsum and ceramic materials which optionally may be coated, e.g. with paint, enamel, polymers and the like. Accordingly the surface may be a member of a system holding, transporting, processing or in contact with aqueous solutions such as water supply systems, food processing systems, cooling systems, chemical processing systems or pharmaceutical processing systems. The inventions is particularly useful for removing biofilm in the wood processing industry, such as the pulp and/or paper industry. Accordingly, the invention is useful in a conventional cleaning-in-place (C-I-P) system. The surface may a member of a system unit such as pipes, tanks, pumps, membranes, filters, heat exchangers, centrifuges, evaporators, mixers, spray towers, valves and reactors. The surface may also be or be a part of utensils used in the medical science and industry such as contaminated endoscopes, prosthetic devices or medical implants.

An important embodiment of the invention is, that the 2,6-β-D-fructan hydrolase of the invention is useful for prevention of so-called bio-corrosion occurring when a metal surface, e.g. a pipeline, is attacked by a microbial biofilm, that is by disintegrating the biofilm the 2,6-β-D-fructan hydrolase prevents the microbial cells of the biofilm from creating a biofilm environment which corrode the metal surface to which it is attached.

Oral Care Applications

The surface may however also be of biological origin such as mucous membranes, skin, teeth, hair, nails etc.

Also teeth with dental plaque, e.g. by incorporating the enzyme of the invention into toothpaste, and contaminated contact lenses are encompasses as surfaces suitable for applying treatment with the 2,6-β-D-fructan hydrolase of the invention. Accordingly the invention includes a process for preparation of a medicament comprising a 2,6-β-D-fructan hydrolase of the invention for disintegration of plaque present on a human or animal tooth. A further use is disintegration of biofilm from mucous membranes such as biofilm in lungs in patients suffering from cystic fibrosis. Accordingly the invention includes a process for preparation of a medicament comprising a 2,6-β-D-fructan hydrolase of the invention for disintegration of a biofilm present on a human or animal mucous membrane.

Accordingly in a still further aspect the present invention relates to an oral care composition comprising a recombinant 2,6-β-D-fructan hydrolase of the invention or a wild-type 2,6-β-D-fructan hydrolases of the invention, preferably purified and essentially free of any active contaminants. An oral care composition of the invention may suitably comprise an amount of a recombinant 2,6-β-D-fructan hydrolase equivalent to an enzyme activity, calculated as enzyme activity units in the final oral care product, in the range from 0.001 LRU to 1000 LRU/ml, preferably from 0.01 LRU/ml to 500 LRU/ml, especially from 0.1 LRU/ml to 100 LRU/ml or 0.5 LRU/ml to 100 LRU LRU/ml.

It is also contemplated according to the invention to include other enzyme activities than 2,6-β-D-fructan hydrolase activity in the oral care composition. Contemplated enzyme activities include activities from the group of enzymes comprising dextranase, mutanases, oxidases, such as glucose oxidase, L-amino acid oxidase, peroxidases, such as e.g. the Coprinus sp. peroxidases described in WO 95/10602 (from Novo Nordisk A/S) or lactoperoxi-dase, haloperoxidases, especially haloperoxidase derivable from Curvularia sp., in particular *C. verruculosa* and *C. inaequalis.*, laccases, proteases, such as papain, acidic protease (e.g. the acidic proteases described in WO 95/02044 (Novo Nordisk A/S)), endoglucosidases, lipases, amylases, including amyloglucosidases, such as AMG (from Novo Nordisk A/S), anti-microbial enzymes, and mixtures thereof.

The oral care composition may have any suitable physical form (i.e. powder, paste, gel, liquid, ointment, tablet etc.). An "oral care composition" can be defined as a composition which can be used for maintaining or improving the oral hygiene in the mouth of humans and animals, by preventing dental caries, preventing the formation of dental plaque and tartar, removing dental plaque and tartar, preventing and/or treating dental diseases etc. At least in the context of the present invention oral care compositions do also encompass products for cleaning dentures, artificial teeth and the like. Examples of such oral care compositions includes toothpaste, dental cream, gel or tooth powder, odontic mouth washes, pre- or post brushing rinse formulations, chewing gum, lozenges, and candy. Tooth pastes and tooth gels typically include abrasive polishing materials, foaming agents, flavoring agents, humectants, binders, thickeners, sweetening agents, whitening/bleaching/stain removing agents, water, and optionally enzymes.

Mouth washes, including plaque removing liquids, typically comprise a water/alcohol solution, flavor, humectant, sweetener, foaming agent, colorant, and optionally enzymes.

Abrasive polishing material might also be incorporated into the oral care composition of the invention such as a dentifrice.

According to the invention said abrasive polishing material includes alumina and hydrates thereof, such as alpha alumina trihydrate, magnesium trisilicate, magnesium carbonate, kaolin, aluminosilicates, such as calcined aluminum silicate and aluminum silicate, calcium carbonate, zirconium silicate, and also powdered plastics, such as polyvinyl chloride, polyamides, polymethyl methacrylate, polystyrene, phenol-formaldehyde resins, melamine-formaldehyde resins, urea-formaldehyde resins, epoxy resins, powdered polyethylene, silica xerogels, hydrogels and aerogels and the like. Also suitable as abrasive agents are calcium pyrophosphate, water-insoluble alkali metaphosphates, dicalcium phosphate and/or its dihydrate, dicalcium orthophosphate, tricalcium phosphate, particulate hydroxyapatite and the like. It is also possible to employ mixtures of these substances.

Dependent on the oral care composition the abrasive product may be present in from to 70% by weight, preferably from 1% to 70%. For tooth pastes the abrasive material content typically lies in the range of from 10% to 70% by weight of the final toothpaste.

Humectants are employed to prevent loss of water from e.g. tooth pastes. Suitable humectants for use in oral care compositions according to the invention include the following compounds and mixtures thereof: glycerol, polyol, sorbitol, polyethylene glycols (PEG), propylene glycol, 1,3-propanediol, 1,4-butanediol, hydrogenated partially hydrolysed polysaccharides and the like. Humectants are in general present in from 0% to 80%, preferably 5 to 70% by weight in toothpaste.

Silica, starch, tragacanth gum, xanthan gum, extracts of Irish moss, alginates, pectin, cellulose derivatives, such as hydroxyethyl cellulose, sodium carboxymethyl cellulose and hydroxypropyl cellulose, polyacrylic acid and its salts, polyvinylpyrrolidone, can be mentioned as examples of suitable thickeners and binders, which helps stabilising a dentifrice product. Thickeners may be present in toothpaste creams and gels in an amount of from 0.1 to 20% by weight, and binders to the extent of from 0.01 to 10% by weight of the final product.

As foaming agent soap, anionic, cationic, non-ionic, amphoteric and/or zwitterionic surfactants can be used. These may be present at levels of from 0% to 15%, preferably from 0.1 to 13%, more preferably from 0.25 to 10% by weight of the final product.

Surfactants are only suitable to the extent that they do not exert an inactivation effect on the present enzymes. Surfactants include fatty alcohol sulphates, salts of sulphonated mono-glycerides or fatty acids having 10 to 20 carbon atoms, fatty acid-albumen condensation products, salts of fatty acids amides and taurines and/or salts of fatty acid esters of isethionic acid.

Suitable sweeteners include saccharin.

Flavours, such as spearmint, are usually present in low amounts, such as from 0.01% to about 5% by weight, especially from 0.1% to 5%.

Whitening/bleaching agents include $H_2O_2$ and may be added in amounts less that 5%, preferably from 0.25 to 4%, calculated on the basis of the weight of the final product.

The whitening/bleaching agents may be an enzyme, such as an oxidoreductase. Examples of suitable teeth bleaching enzymes are described in WO 97/06775 (from Novo Nordisk A/S).

Water is usually added in an amount giving e.g. toothpaste a flowable form.

Further water-soluble anti-bacterial agents, such as chlorhexidine digluconate, hexetidine, alexidine, Triclosan®, quaternary ammonium anti-bacterial compounds and water-soluble sources of certain metal, ions such as zinc, copper, silver and stannous (e.g. zinc, copper and stannous chloride, and silver nitrate) may also be included.

Also contemplated according to the invention is the addition of compounds which can be used as fluoride source, dyes/colorants, preservatives, vitamins, pH-adjusting agents, anti-caries agents, desensitizing agents etc.

Other components useful in oral care compositions of the invention are enzymes as described supra. Enzymes are biological catalysts of chemical reactions in living systems. Enzymes combine with the substrates on which they act forming an intermediate enzyme-substrate complex. This complex is then converted to a reaction product and a liberated enzyme which continue its specific enzymatic function.

Enzymes provide several benefits when used for cleansing of the oral cavity. Proteases break down salivary proteins, which are adsorbed onto the tooth surface and form the pellicle, the first layer of resulting plaque. Proteases along with lipases destroy bacteria by lysing proteins and lipids which form the structural components of bacterial cell walls and membranes.

Dextranase and other carbohydrases such as the 2,6-β-D-fructan hydrolase of the invention breaks down the organic skeletal structure produced by bacteria that forms a matrix for bacterial adhesion. Proteases and amylases, not only prevents plaque formation, but also prevents the development of calculus by breaking-up the carbohydrate-protein complex that binds calcium, preventing mineralization.

A toothpaste of the invention may typically comprise the following ingredients (in weight % of the final toothpaste composition):

Abrasive material 10 to 70%

Humectant 0 to 80%

Thickener 0.1 to 20%

Binder 0.01 to 10%

Sweetener 0.1% to 5%

Foaming agent 0 to 15%

Whitener 0 to 5%

Enzymes 0.0001% to 20%

In a specific embodiment a tooth paste of the invention has a pH in the range from 6.0 to about 8.0, and comprises:

a) 10% to 70% Abrasive material b) 0 to 80%Humectant c) 0.1 to 20%Thickener d) 0.01 to 10%Binder e) 0.1% to 5%Sweetener f) 0 to 15%Foaming agent g) 0 to 5%Whitener i) 0.0001% to 20%Enzymes.

Said enzymes referred to under i) include a recombinant 2,6-β-D-fructan hydrolase of the invention, and optionally other types of enzymes mentioned above known to be used in toothpastes and the like.

A mouth wash of the invention may typically comprise the following ingredients (in weight % of the final mouth wash composition):

0–20%Humectant

0–2% Surfactant

0–5% Enzymes

0–20%Ethanol

0–2% Other ingredients (e.g. flavour, sweetener active ingredients such as florides).

0–70%Water

The mouth wash composition may be buffered with an appropriate buffer e.g. sodium citrate or phosphate in the pH-range 6–7.5.

The mouth wash may be in none-diluted form (i.e. must be diluted before use).

The oral care compositions of the invention may be produced using any conventional method known to the art of oral care.

Detergent Applications

In another preferred embodiment the 2,6-β-D-fructan hydrolase of the invention may also be incorporated in detergent compositions and used for removal/cleaning of biofilm present on household and/or industrial textile/laundry. Accordingly the 2,6-β-D-fructan hydrolase of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the 2,6-β-D-fructan hydrolase of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts. Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include Alcalase™, Savinase™, Primase™, Duralase™, Esperase™, and Kannase™ (Novo Nordisk A/S), Maxatase™, Maxacal™, Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from Humicola (synonym Thermomyces), e.g. from H. lanuginosa (T. lanuginosus) as described in EP 258 068 and EP 305 216 or from H. insolens as described in WO 96/13580, a Pseudomonas lipase, e.g. from P. alcaligenes or P. pseudoalcaligenes (EP 218 272), P. cepacia (EP 331 376), P. stutzeri (GB 1,372,034), P. fluorescens, Pseudomonas sp. strain SD 705 (WO 95/06720 and WO 96/27002), P. wisconsinensis (WO 96/12012), a Bacillus lipase, e.g. from B. subtilis (Dartois et al. (1993), Biochemica et Biophysica Acta, 1131, 253–360), B. stearothermophilus (JP 64/744992) or B. pumilus (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novo Nordisk A/S). Amylases: Suitable amylases (α and/or β) include those of bacterial or fungal origin. Chemically modified or protein engineered mutants are included. Amylases include, for example, α-amylases obtained from Bacillus, e.g. a special strain of B. licheniformis, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novo Nordisk A/S), Rapidase™ and Purastar™ (from Genencor International Inc.). Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g. the fungal cellulases produced from Humicola insolens, Myceliophthora thermophila and Fusarium oxysporum disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme™, and Carezyme™ (Novo Nordisk A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from Coprinus, e.g. from C. cinereus, and variants thereof as those described in WO 93/24618, WO 95/10602, and WO 98/15257.

Commercially available peroxidases include Guardzyme™ (Novo Nordisk A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0–30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0–65% of a detergent builder or complexing agent such as zeolite, diphosphate, triphosphate, phosphonate, carbonate citrate, nitrilotriacetic acid, ethylenediaminetetraacetic acid, diethylenetriamine-pentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesultonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01–100 mg of enzyme protein per liter of wash liqour, preferably 0.05–5 mg of enzyme protein per liter of wash liqour, in particular 0.1–1 mg of enzyme protein per liter of wash liqour.

The enzyme of the invention may additionally be incorporated in the detergent formulations disclosed in WO 97/07202 which is hereby incorporated as reference.

Production of 2,6-β-D-fructose Oligosaccharide Sweeteners

The 2,6-β-D-fructan hydrolase of the invention is also useful in a hydrolysis process of levan and phlein, with the purpose of generating β2,6-fructose oligosaccharides. β-2,6-fructose oligosaccharides are useful as sweeteners in foods and exhibit or have additionally positive health effects. The benefits of oligosaccharide ingestion such as a) proliferation of Bifidobacteria and reduction of detrimental bacteria, b) reduction of toxic metabolites and detrimental enzymes, c) prevention of pathogenic and autogenous diarrhea, d) prevention of constipation, e) protecktion of liver function, f) reduction of blood pressure, g) anti cancer effect, h) production of nutrients and i) replacement of antibiotics in feed are described in Tomomatsu H; Food technology; 1994; vol. 48, pp. 61–65.

Accordingly an embodiment of the invention is a process for production of β-2,6-fructose oligosaccharides comprising contacting a material comprising a substrate selected from the group consisting of levan and phlein with the 2,6-β-D-fructan hydrolase of the invention in an aqueous medium, the 2,6-β-D-fructan hydrolase being, present in an amount sufficient to hydrolyze the substrate.

A suitable phlein comprising material may be a plant material suitable for the process or purified phlein recovered from processing such a plant material. A preferred plant material is a grass, preferably off the order of graminales (Poales), e.g. *Dactylis glomerata* (orchard grass), *Festuca arundinacea, Lolium temulentum, Lolium multiflorum, Lolium perenne* (Perennial ryegrass), *Phleum pratense* as well as Rye (Secale), Oat (Aveneae), Wheat (Triticeae), Barley (Hordeum) and rice (Oryzeae) and bamboo (Bambuseaea). Both stems and/or leafs of grasses contains phlein. Grasses has so far found little applicability in producing food additives.

The plant material comprising the phlein may be preprocessed prior to the enzyme reaction, i.e. after harvesting it may be cut into small pieces (shredded), followed by maceration to open the cells. Maceration may be accomplished by using conventional physical methods and/or cell wall degrading enzymes known to the art. The material may be further processed to recover a purified phlein, e.g. separating the soluble phlein from insoluble fractions of the material by extraction. The phlein may be further purified by separating phlein from proteins by precipitating the proteins e.g. by acid or salt precipitation followed by centrifugation.

The phlein may be even further purified by precipitating the phlein, e.g. by adding an alcohol, e.g. ethanol, to the phlein solution.

The phlein comprised in the plant material or the purified phlein is then subjected to hydrolysis with a 2,6-β-D-fructan hydrolase of the invention optionally in combination one or more other hydolases such as inulinases (EC 3.2.1.7), fructan β-fructosidases (EC 3.2.1.80), and levanbiohydrolases (EC 3.2.1.64.)

The hydrolysis reaction producing β-2,6-fructose oligosaccharides should be carried out at conditions allowing a suitable activity level of the 2,6-β-D-fructan hydrolase:

Accordingly the hydrolysis reaction should preferably be carried out at a pH in the range of from about pH 4 to about pH 8, in particular of from about pH 5 to about pH 7.

Further the hydrolysis reaction should preferably be carried out at a temperature of from about 10° C. to about 70° C., more preferred of from about 20° C. to about 50° C., most preferred of from about 30° C. to about 40° C., e.g. 37° C.

The reaction time depends on the material comprising the levan or phlein and may be any time suitable for obtaining the desired degree of hydrolysis. Usually a reaction time within about 1 to 72 hours is suitable. A preferred reaction time is about 10 to 48 hours, more preferred about 15–35 hours most preferred 20–30 hour, e.g. 24 hours overnight reaction.

The 2,6-β-D-fructan hydrolase of the invention should be dosed in amounts sufficient for achieving the desired degree of hydrolysis within the desired reaction time. It is at present contemplated that a suitable enzyme dosage is in the range of from 0.00001–100 is suitable depending on the amount, origin and purity of the substrate. A more preferred dosage is 0.0001–10 mg/l, while 0.001–1 mg/l, e.g. 0.1 mg/l is most preferred.

Production of Fructose

Fructose may be produced by as a first step degrading a substrate selected from phlein or levan with the enzyme of the invention, and as a second step either subsequently or simultaneously contacting the generated 2,6-β-D-fructose oligosaccharides with an 2,6-β-D-fructan exo-hydrolase, such as sacC exo-levanase from *Bacillus subtillis* e.g. as described in Wanker E., Huber A., Schwab H.; *Purification and characterization of Bacillus subtillis levanase produced in Escherichia coli*, Applied and environmental microbiology, 1995, vol. 61, no. 5, pp. 1953–1958.

Materials and Methods

General Molecular Biology Methods

Unless otherwise mentioned the DNA manipulations and transformations were performed using standard methods of molecular biology (Sambrook et al. (1989) supra; Ausubel, F. M. et al. (eds.); *Current protocols in Molecular Biology;* 1995; John Wiley and Sons.; Harwood C. R., and Cutting S. M. (eds.); *Molecular Biological Methods for Bacillus;* 1990; John Wiley and Sons.

Media

TY medium was prepared as described in Ausubel et al. (1995), supra.

Diluted TY-medium was prepared by diluting TY medium 1:10 with demineralized water.

Diluted TY medium supplemented with stained levan. This medium was prepared by adding a 10% w/w stained levan solution to the diluted TY medium at a ratio of 20 ml stained levan solution to 500 ml diluted TY medium. The levan was stained according to the description in Rinderknecht H., Wilding P., Haverback B. J. Experientia, 1967, vol. 23, p 805.

B-medium was prepared as described in Bertani G.; J. Bacteriol.; 1951; vol. 62!; pp. 293–300. BPX medium was prepared in accordance with EP 0 506 780 (WO 91/09129). BPG medium was prepared by mixing 500 ml of LB medium with 5 ml phosphate buffer, 1 M, adjusted to pH 7 and 10 ml 20% w/w aqueous glucose solution.

Deposited Organisms

The following microorganisms was deposited by the inventors according to the Budapest Treaty on the International Recognition of the Deposit of Microorganisms for the Purposes of Patent Procedure at the Deutsche Sammlung von Mikroorganismen und Zellkulturen GmbH, Mascheroder Weg 1b, D-38124 Braunschweig, Federal Republic of Germany:

Deposition number DSM 12458; *Paenibacillus amylolyticus;* Oct. 23, 1998.

Deposition number DSM 12406; *E. coli* harboring strain transformed with plasmid pSJ1678 containing a nucleic acid sequence encoding a 2,6-β-D-fructan hydrolase polypeptide; Oct. 23, 1998.

Deposition number DSM 13026; *Paenibacillus pabuli;* Sep. 8, 1999.

Deposition number DSM 13029; *E. coli* harboring strain transformed with plasmid pSJ1678 containing a nucleic acid sequence encoding a 2,6-β-D-fructan hydrolase polypeptide; Sep. 8, 1999.

Deposition number DSM 13025; *Paenibacillus macerans;* Sep. 8, 1999.

Deposition number DSM 13028; *E. coli* harboring strain transformed with plasmid pSJ1678 containing the nucleic acid sequence encoding a 2,6-β-D-fructan hydrolase polypeptide; Sep. 8, 1999.

Other Organisms

Host cells were cells of *E. coli* SJ2 (Diderichsen B., Wedsted U., Hedegaard L., Jensen B. R., Sjøholm C.; *Cloning of aldB, which encodes alpha-acetolactate decarboxylase, an exoenzyme from Bacillus brevis;* J. Bacteriol., 1990, vol. 172, pp. 4315–4321).

acillus subtilis strain SHa273 disclosed in WO 95/10603 was used. Competent cells were prepared and transformed as described by Yasbin, R. E., Wilson, G. A. and Young, F. E. (1975) Transformation and transfection in lysogenic strains of *Bacillus subtilis:* evidence for selective induction of prophage in competent cells. J. Bacteriol, 121:296–304.

Plasmids

SJ1678 as described in the International Patent Application published as WO 94/19454 which is hereby incorporated by reference in its entirety.

pLi937 is pSJ1678 with an insert containing SEQ ID No:2.

pMOL944. This plasmid is a pUB110 derivative essentially containing elements making the plasmid propagatable in *Bacillus subtilis,* kanamycin resistance gene and having a strong promoter and signal peptide cloned from the amyL gene of *B. licheniformis* ATCC14580. The signal peptide contains a SacII site making it convenient to clone the DNA encoding the mature part of a protein in-fusion with the signal peptide. This results in the expression of a Pre-protein which is directed towards the exterior of the cell. The plasmid was constructed by means of ordinary genetic engineering and is briefly described in the following. The pUB110 plasmid (McKenzie, T. et al., 1986, Plasmid 15:93–103) was digested with the unique restriction enzyme NciI. A PCR fragment amplified from the amyL promoter encoded on the plasmid pDN1981 (P. L. Jørgensen et al.,1990, Gene, 96, p37–41.) was digested with NciI and inserted in the NciI digested pUB110 to give the plasmid pSJ2624.

The two PCR primers used have the following sequences:

\# LWN5494 5'-GTCGCCGGGGCGGCCGCTATCAATTGGTAACTGTATCTCAGC-3'

\# LWN5495 5'-GTCGCCCGGGAGCTCTGATCAGGTACCAAGCTTGTCGACCTGCAGAATGAGGCAGCAAGAAGAT-3'

The primer #LWN5494 inserts a NotI site in the plasmid. The plasmid pSJ2624 was then digested with SacI and NotI and a new PCR fragment amplified on amyL promoter encoded on the pDN1981 was digested with SacI and NotI and this DNA fragment was inserted in the SacI-NotI digested pSJ2624 to give the plasmid pSJ2670. This cloning replaces the first amyL promoter cloning with the same promoter but in the opposite direction. The two primers used for PCR amplification have the following sequences:

\#LWN5938 5'-GTCGGCGGCCGCTGATCACGTAC-

CAAGCTTGTCGACCTGCAGAATG
AGGCAGCAAGAAGAT-3'
LWN5939 5'-
GTCGGAGCTCTATCAATTGGTAACTGTATCTCA
GC-3'

The plasmid pSJ2670 was digested with the restriction enzymes PstI and BclI and a PCR fragment amplified from a cloned DNA sequence encoding the alkaline amylase SP722 (Patent # WO9526397-A1) was digested with PstI and BclI and inserted to give the plasmid pMOL944. The two primers used for PCR amplification have the following sequence:

LWN7864 5'-
AACAGCTGATCACGACTGATCTTTTAGCTTGG
CAC-3'
LWN7901
5'-AACTGCAGCCGCGGCACATCATAATGGGACA
AATGGG-3'

The primer #LWN7901 inserts a SacII site in the plasmid.
Isolation of Genomic DNA The strains of Paenibacillus DSM 12458, DSM 13026 and DSM 13025 were propagated in liquid TY medium. After 16 hours incubation at 37° C. and 300 rpm, the cells were harvested, and genomic DNA isolated by the method described by Pitcher D. G., Saunders N. A., Owen R. J.; *Rapid extraction of bacterial genomic DNA with guanidium thiocyanate;* Lett. Appl. Microbiol.; 1989; vol. 8; pp. 151–156.

Genomic Library Construction

Genomic DNA was partially digested with restriction enzyme Sau3A, and size-fractionated by electrophoresis on a 0.7% agarose gel. Fragments between 2 and 10 kb in size was isolated by electrophoresis onto DEAE-cellulose paper (Dretzen G., Bellard M., Sassone-Corsi P., Chambon P.; *A reliable method for the recovery of DNA fragments from agarose and acrylamide gels;* Anal. Biochem.; 1981; vol. 112; pp. 295–298).

Isolated DNA fragments were ligated to BamHI digested pSJ1678 plasmid DNA, and the ligation mixture was used to transform *E. coli* SJ2.

Transformation

*E. coli* SJ2 host cells were prepared for and transformed by electroporation using a gene PULSER™ electroporator from BIO-RAD as described by the supplier.

Identification of Positive Transformant

A DNA library in *E. coli* SJ2, constructed as described above, was screened on agar plates made of ten times diluted TY-medium or undiluted LB medium, supplemented with stained levan and incubated overnight at 37° C. For clones/colonies expressing the 2,6-β-D-fructan hydrolase clearing zones (decoloration of the stained levan) appeared.

Isolation of the DNA Sequence Shown in SEQ ID No: 2, SEQ ID No: 4 and SEQ ID No: 6

Positive *E. coli* transformants found, DSM 12406, DSM 13029 and DSM 13028 and the nucleic acid sequences shown in SEQ ID NO: 2, SEQ ID No: 4 and SEQ ID No: 6 encoding the 2,6-β-D-fructan hydrolase of the invention were obtained by extraction of plasmid DNA by methods known in the art (Sambrook et al. (1989) supra.

Sequencing the DNA Encoding the 2,6-β-D-fructan Hydrolase

The DNA encoding 2,6-β-D-fructan hydrolase of the invention was sequenced by conventional methods known to the art, i.e. by DNA sequencing of the cloned Sau3A DNA fragment. The DNA was characterised by DNA sequencing using the Taq deoxy-terminal cycle sequencing kit (Perkin-Elmer, USA), fluorescent labelled terminators and appropriate oligonucleotides as primers.

SDS-PAGE Gel Electrophoresis

The SDS-PAGE characterization of the 2,6-β-D-fructan hydrolase was performed according to methods known to the art (Sambrook et al. (1989) supra). The electrophoresis was performed on a 4–20% gradient Tris-Glycine precast gel (catalog no. EC60255; NOVEX Electrophoresis GmbH, D-65929 Frankfurt/M.) according to the instructions enclosed with the product on a Laemmli-type, Tris-glycine, SDS-PAGE, denaturing and reducing gel. After electrophoresis, the gel is stained with GelCode Blue Stain Reagent (catalog no. 24590; Pierce Chemical Company, Rockford Ill., USA) according to the instructions enclosed with the reagent. As molecular weight standards on the SDS-PAGE gel, an Electrophoresis Calibration Kit (catalog no. 17-0446-01; Amersham Pharmacia, Uppsala, Sweden) was used with molecular weights: 94,000; 67,000; 43,000; 30,000; 20,100 and 14,400.

Determination of Protein by BCA Protein Assay

This assay is identical to PIERCE cat. No. 23225 Pierce Chemical Company, Rockford Ill., USA: BCA protein assay kit, and the assay was performed according to the description provided with the kit. The BCA working solution was made by mixing 50 parts of reagent A with 1 part reagent B. 200 µl enzyme sample and standard solutions of BSA was each mixed with 2.0 ml BCA working solution. After 30 minutes at 37° C., the sample and standards was cooled to room temperature and $OD_{490}$ was read. $OD_{490}$ of the enzyme sample was compared with the $OD_{490}$ of the BSA standards by interpolation as a measure of the protein concentration (in mg enzyme per ml) in the sample.

2,6-β-D-fructan Hydrolase Activity Assay

The following assay was used for characterization of the 2,6-β-D-fructan hydrolase. The principle of the assay is that 2,6-β-D-fructan hydrolase hydrolyzes levan thereby generating reducing groups. The increase in reducing ends generated after an incubation, which is a measure of the 2,6-β-D-fructan hydrolase activity, is monitored by adding a reagent forming a color upon reaction with the reducing groups. To correlate the color formation to the amount of generated reducing groups the optical density or absorbance is compared to the color formation of standard samples of fructose with a predetermined number of reducing groups.

1 LRU (Levan Reducing sugar Unit) is defined as the amount of enzyme that generates an amount of reducing groups in a levan substrate equivalent to 1 µmol fructose per minute.

Procedure

A buffer (A) is prepared consisting of 50 mM $CH_3COOH$, 50 mM $KH_2PO_4$, 50 mM $H_3BO_3$, 1 mM $CaCl_2$, 1 mM $MgCl_2$ and 0.01% Triton X-100. The solution adjusted to pH-value 6.5 with a solution of hydrochloric acid or sodium hydroxide.

A levan substrate solution (B) is prepared by dissolving 15 mg/ml levan (Sigma, L-8647) in the buffer (A).

A sample solution (C) is prepared by dissolving/diluting a sample of recovered 2,6-β-D-fructan hydrolase in the buffer (B).

A CNC-reagent (D) is prepared by mixing in the following order: 1.8 ml demineralized water, 200 µl 40 mM $CuSO_4$, 6.0 ml 0.67 mg/ml Neocuproin-HCl (Merck 2964) and 2.67 ml 2.0 M $Na_2CO_3$. The CNC-reagent was made just before use.

A mixture of 50 µl levan substrate (B) and 25 µl enzyme sample (C), a mixture of 50 µl levan substrate (B) and 25 µl buffer (A) and fructose standard solutions are transferred to ice cooled Eppendorf tubes. Incubation is initiated by placing the tubes in an Eppendorf thermomixer at 37° C. The tubes is incubated for 15 minutes on the Eppendorf thermomixer with shaking. The incubation is stopped by ice cooling the tubes, adding 500 μl ice-cold CNC-reagent (D), and mixing the solutions in the tubes by sucking back and forth the solutions with a pipette. To develop the color, the tubes is placed in an Eppendorf thermomixer and incubated for 30 minutes at 25° C. without exposing the tubes to light. 200 μl of the colored solutions is transferred to a microtiter plate and $OD_{450}$ is read. $OD_{450}$ for the solution containing both enzyme and levan minus $OD_{450}$ for the solution containing only levan is compared to the $OD_{450}$ for the standards containing fructose only by interpolation.

EXAMPLES

The invention is further illustrated with the following examples which are not, in any way, intended to be limiting to the scope of the invention as claimed.

Example 1

Culturing of Paenibacillus amylolyticus DSM 12458

DSM 12458 was grown in a TY medium, pH 7.0, supplemented with 0.2% w/w levan at 30° C. Culture supernatant was harvested on day 1, 2, and 5, respectively and centrifuged 10 minutes in Eppendorf Cups. An agarose gel plates containing 20 ml 10% w/w stained levan solution per 500 ml agarose gel was casted. 20 μl cell free supernatant samples were applied to 4 mm holes which were punched out of the agarose gel plates. The agarose gel plates were incubated at 37° C. for 2 hours. For all harvested samples clearing zones appeared around the holes showing presence of the 2,6-β-D-fructan hydrolase in the supernatant already from the first harvesting day.

Example 2

Degradation of Levan with the 2,6-β-D-fructan Hydrolase

Enzyme was recovered from the culture supernatant of example 1 by gel filtration of the supernatant on a Sephadex G25 PD-10 column kit at conditions according to instruction by supplier (Pharmacia). The enzyme was eluted using a 0.02 M MOPS buffer at pH 7.0. 0.4 ml of the recovered enzyme preparation was mixed with 0.4 ml of a 2% w/w levan solution and 0.2 ml buffer (0.1 M Na-acetate buffer pH 5.5). One sample of 0.5 ml was taken immediately after preparation and the enzyme reaction was stopped by boiling for 20 minutes and centrifugation. Another sample of 0.5 ml was incubated overnight at 30° C., where after the enzyme reaction was stopped. Both samples were analyzed by Dionex HPLC analysis.

The analysis showed that during the incubation overnight the levan was almost totally degraded into 2,6-β-fructose oligo saccharides and fructose indicating that the 2,6-β-D-fructan hydrolase is an endo-hydrolase.

Example 3

Culturing of E. coli DSM 12406 and Recovery and Purification of Cloned 2,6-β-D-fructan Hydrolase DSM 12406 grown in a TY medium, pH 7.0, supplemented with 0.2% w/w levan at 30° C. for 24 hours. 5 litres of supernatant was filtered through a Seitz EKS depth filter plate to give a germ free filtrate. The pH in the germ free filtrate was adjusted to pH 7.0 with $CH_3COOH$ and diluted to 50 L with demineralized water. The conductivity was 2.3 rmS/cm. The enzyme solution was applied to a 1 litre Q-sepharose FF column equilibrated in 10 mM $KH_2PO_4$/NaOH, pH 7.0. After washing the column with the equilibration buffer, the 2,6-β-D-fructan hydrolase was eluted with a linear NaCl gradient (0→0.5M). 2,6-β-D-fructan hydrolase containing fractions were pooled and $(NH_4)_2SO_4$ was added to 2.0M final concentration. The enzyme was applied to a 100 ml Butyl Toyopearl 650S column equilibrated in 10 mM $KH_2PO_4$/NaOH, pH 7.0, 2M $(NH_4)_2SO_4$, pH 7.0. After washing the column with the equilibration buffer, the 2,6-β-D-fructan hydrolase was eluted with a linear $(NH_4)_2SO_4$ gradient (2→0M). 2,6-β-D-fructan hydrolase containing fractions were pooled and the buffer was exchanged with 10 mM $KH_2PO_4$/NaOH, pH 7.0 on a Sephadex G25 column. The G25 filtrate was applied to a 40 ml SOURCE 30Q column equilibrated in 10 mM $KH_2PO_4$/NaOH, pH 7.0. The column was washed with the equilibration buffer and the 2,6-β-D-fructan hydrolase was eluted with a linear NaCl gradient (0→0.3M). 2,6-β-D-fructan hydrolase containing fractions were analysed by SDS-PAGE as shown in FIG. 1 and the molecular weight of the levanase (band (1)) was determined to be about $M_r$=88 kDa by interpolation. The N-terminus of the prepared 2,6-→-D-fructan hydrolase was found to be blocked. Less than 1 mg 2,6-β-D-fructan hydrolase was purified from the 5 litres of culture supernatant.

Example 4

Determination of Dose-response

Figure 2:
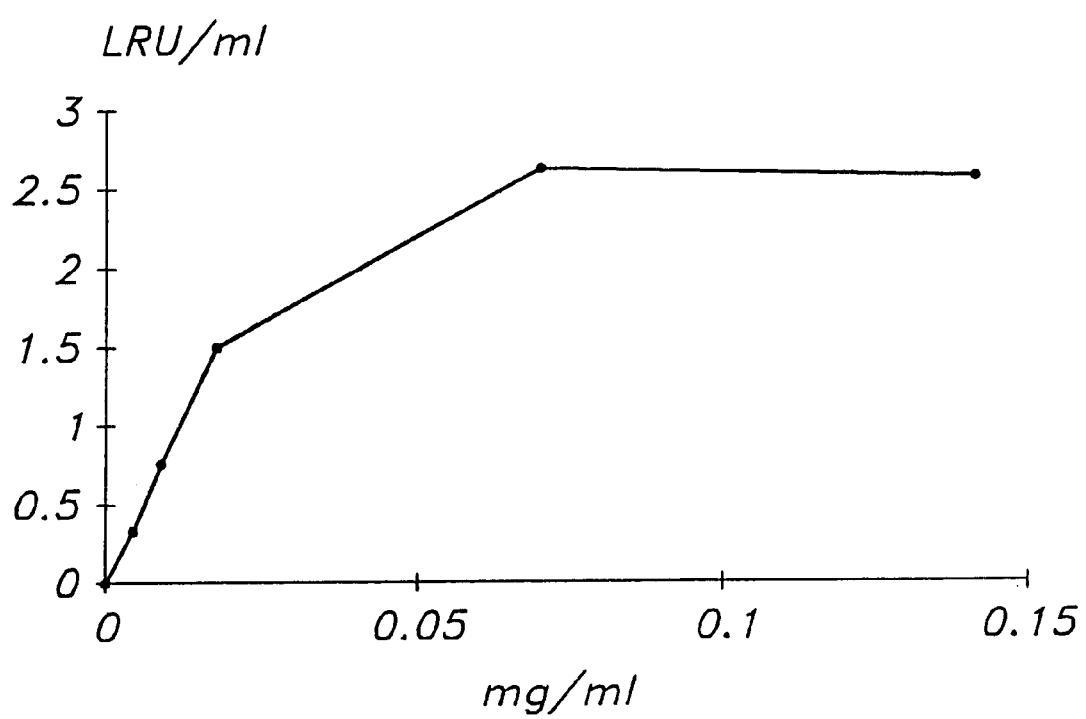
FIG. 2 shows the dose-response relation between dosed 2,6-β-D-fructan hydrolase of the mature part of SEQ ID No:1 and the response in the LRU assay.

The relation between amount of 2,6-β-D-fructan hydrolase enzyme protein and the measured response in the 2,6-β-D-fructan hydrolase assay was determined. Determination of the dose-response relation was determined by subjecting samples of various enzyme protein concentration to the 2,6-β-D-fructan hydrolase assay, and the result is shown in FIG. 2. It is observed that the 2,6-β-D-fructan hydrolase assay is linear between 0 and approx. 1.5 LRU/ml, which range was used throughout further analyses.

Example 5

Figure 3:
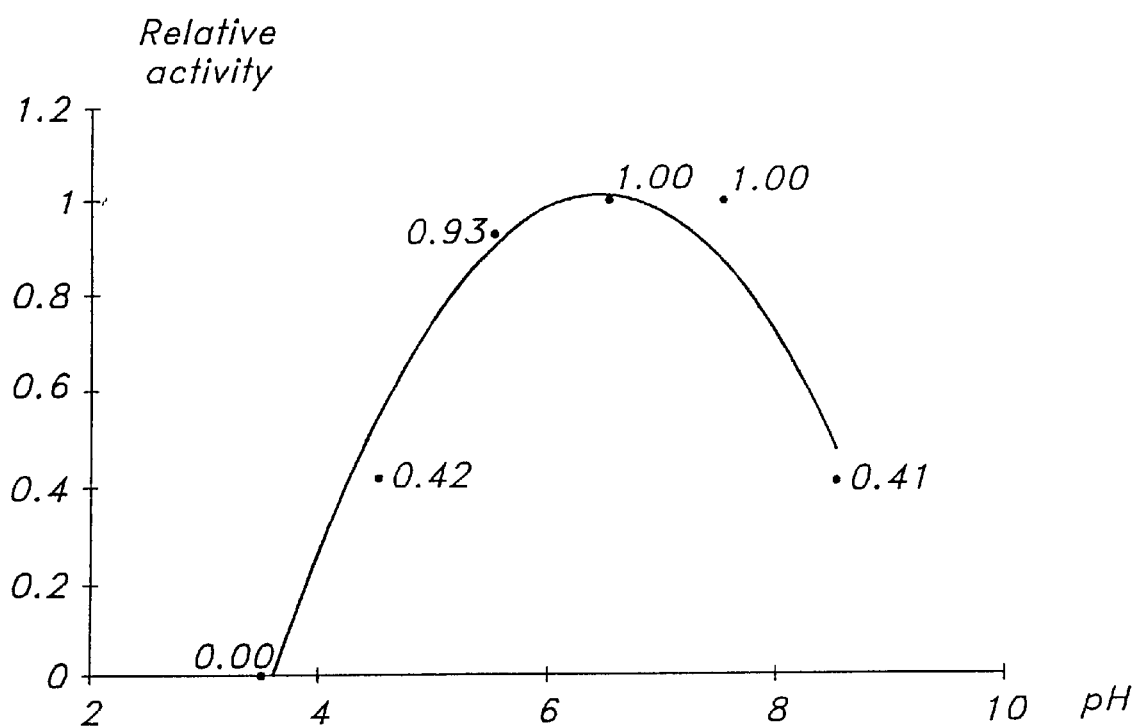
FIG. 3 shows the relation between activity of the 2,6-β-D-fructan hydrolase of the mature part of SEQ ID No:1 and the pH in the LRU assay medium at 37° C.

Determination of pH-activity Range 2,6-β-D-fructan hydrolase activities were determined in the 2,6-β-D-fructan hydrolase assay at 37° C. and at pH-values 3.5 to 8.5, buffers being pH adjusted with either HCl or NaOH. The reults were plotted as activities relative to the maximum activity against the pH-value as shown in FIG. 3. It was observed from the result that the 2,6-β-D-fructan hydrolase has a near neutral optimum between pH 6.5 and 7.0. In addition, 2,6-β-D-fructan hydrolase samples were preincubated for 2 hours at 37° C. at the different pH-values with less than 10% reduction in activity. Accordingly 2,6-β-D-fructan hydrolase is found fairly stable in the pH range 4.5 to 8.5.

Example 6

Figure 4:
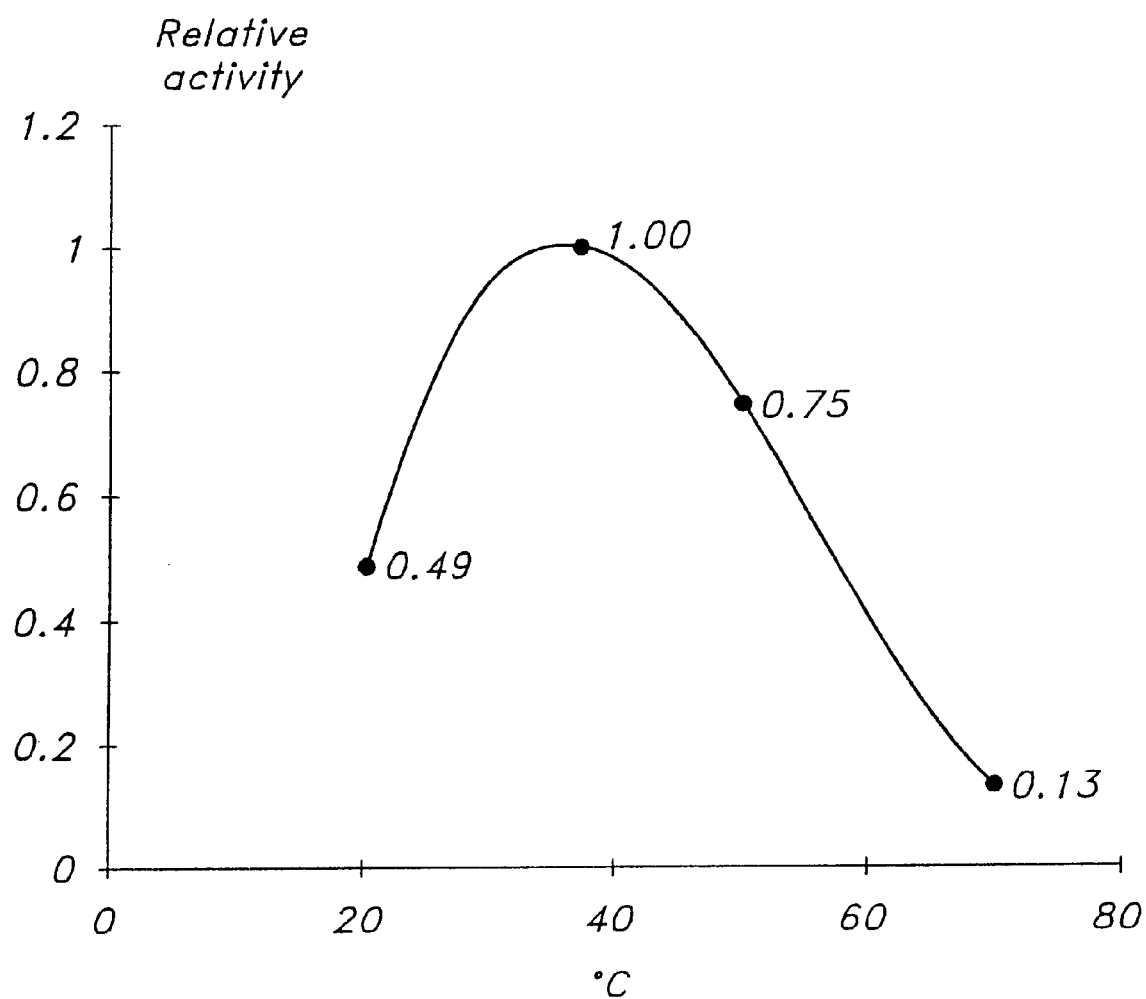
FIG. 4 shows the relation between activity of the 2,6-β-D-fructan hydrolase of the mature part of SEQ ID No:1 and the temperature in the LRU assay medium at pH 6.5.

Determination of Temperature-activity Range 2,6-β-D-fructan hydrolase activities were determined in the 2,6-β-D-fructan hydrolase assay at pH 6.5 and at temperatures 20° C., 37° C., 50° C., and 70° C. The results were plotted as activities relative to the maximum activity against the temperature as shown in FIG. 4. It was observed that the 2,6-β-D-fructan hydrolase has a temperature optimum at about 37° C.

Example 7

Biofilm Disintegration by 2,6-β-D-fructan Hydrolase and Combined Systems Containing 2,6-β-D-fructan Hydrolase Biofilm was made on stainless steel, and activity of enzymes against microbial biofilm was determined as a release of biofilm from the surface.

A preculture is made by mixing 220 ml tap-water with 10 ml Tryptone Soya Broth (TSB, Oxoid CM129), the water was incubated for 48 hours at approximately 20° C. The culture was then re-circulated, by use of a peristaltic pump, through a modified Robbins Device with 25 steel plugs holding 25 steel discs. After 3 days, diluted substrate (1/7 TSB+glucose 1 g/L) was added continuously to the culture during 48 hours as the culture was circulated trough the Robbins Device.

Biofilm with microorganisms from tap-water was formed on the steel discs in the Robbins Device. The effects of enzymes against this biofilm was evaluated in two ways: a) by removing all discs from the Robbins Device and performing the enzyme treatment in a micro-titer plate (24 wells, pH 6.5, 50° C. for 2 hours) or b) by making a biofilm in two Robbins devices with a serial connection, so that an identical biofilm was made in both devices. The Robbins devices was kept assembled and the enzyme solution (pH 6.5, 50° C. for 2 hours), was circulated through one of the Devices and a control solution without enzyme is circulated through the other device. After the enzyme treatment all discs were removed from the Robbins devices and the enzyme effect was evaluated.

The amount of biofilm left on the steel surface was evaluated either by fluorescent microscopy where all microbial cells on the surface were stained with a fluorescent dye (DAPI), or by conductance measurements.

Fluorescence Microscopy

The DNA-binding fluorochrome DAPI (4',6-diamidino-2-phenylindole, Sigma D-9542) was used as an indicator for the total cell number. The discs with biofilm were after enzyme treatment incubated in the dark for 5 min with DAPI (3 mM). The stained cells were examined under a 100× magnification oil immersion fluorescence objective on an Olympus model BX50 microscope equipped with a 200 W mercury burner. The filter combination used for viewing DAPI-stained cells was a 330–385 nm excitation filter and a 420 barrier filter (Olympus cube model U-MWU).

Conductance Measurements

Indirect Malthus measurements were used when enumerating adherent cells on the substrata (Johnston M. and Jones M. V.; *Disinfection tests with intact biofilms: combined use of the modified Robbins Device with impedance detection;* J. Microbiol., 1995; Methods 21; pp.15–26; Johansen C., Falholt P. and Gram L.; *Enzymatic removal and disinfection of bacterial biofilms;* Appl. Environ. Microbiol.; 1997; vol. 63; pp. 3724–3728). The discs were after incubation with enzymes transferred to Malthus tubes containing 3 ml of growth media (TSB) in the outer tube and 0.5 ml 0.1 M KOH in the inner tube (Dezenclos T., Ascon-Cabrera M., Ascon D., Lebeault J.-M. and Pauss A.; *Optimisation of the indirect impedancemetry technique; a handy technique for microbial growth measurements;* Appl. Microbiol. Biotechnol.; 1994; vol. 42; pp. 232–238). Tubes were placed in a Malthus 2000 (Malthus Flexi 2000, Malthus Instrument FLimited) and incubated at 25° C.

Carbon dioxide produced by the bacteria were absorbed by the KOH and thereby altering the conductivity. Changes in conductance were plotted against time and the detection time (DT) was determined as the time taken from start of the measurement until a rapid change in conductance was detecable by the Malthus. The DT was related to the number of cells present at the start of the test by use of a calibration curve, which was constructed for each organism by inoculating Malthus tubes with a tenfold dilution series (Johansen et al. 1997, supra).

Biofilm removal by the recombinant 2,6-β-D-fructan hydrolase was evaluated both for the 2,6-β-D-fructan hydrolase alone and in combination with other enzyme activities by combining with BioCip-membrane. BioCip-membrane (Novo Nordisk A/S, Denmark) is a commercially available multicomponent enzyme preparation containing protease activity and a wide range of carbo-hydrases including cellulase, arabanase, hemi-cellulase, β-glucanase, pectinases and xylanase activities.

Figure 5:
FIG. 5 shows microscopy photos of steel surfaces with biofilm, cleaned with or without the 2,6-β-D-fructan hydrolase of the mature part of SEQ ID No:1.
Figure 5:
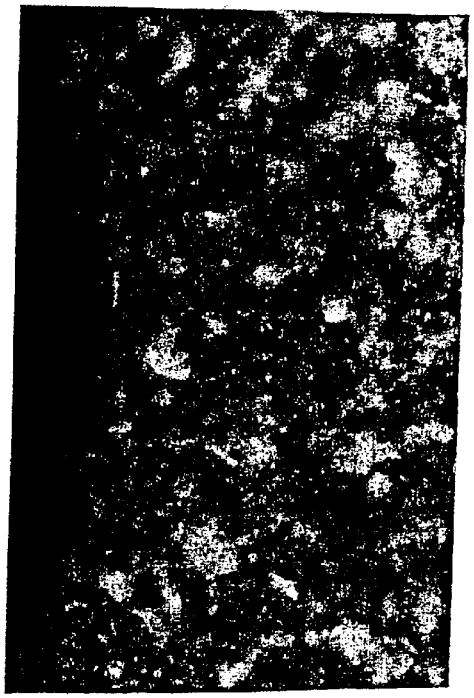
Figure 5:
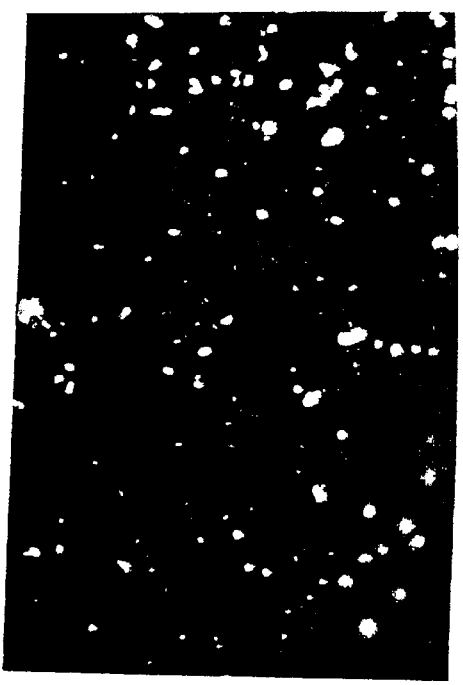
Figure 5:

A significant removal of biofilm was observed by microscopy (FIG. 5), both when 2,6-β-D-fructan hydrolase was used alone and when used in combination with Bio-Cip membrane. FIG. 5 shows DAPI staining of microbial cells on steel surfaces. 1) and 2) are the control biofilms which are cleaned without enzymes, and 3) and 4) are the same biofilm cleaned with 2,6-b-D-fructan hydrolase (10 mg/L) for 2 hours at 50° C. and pH 6.5.

Figure 6:
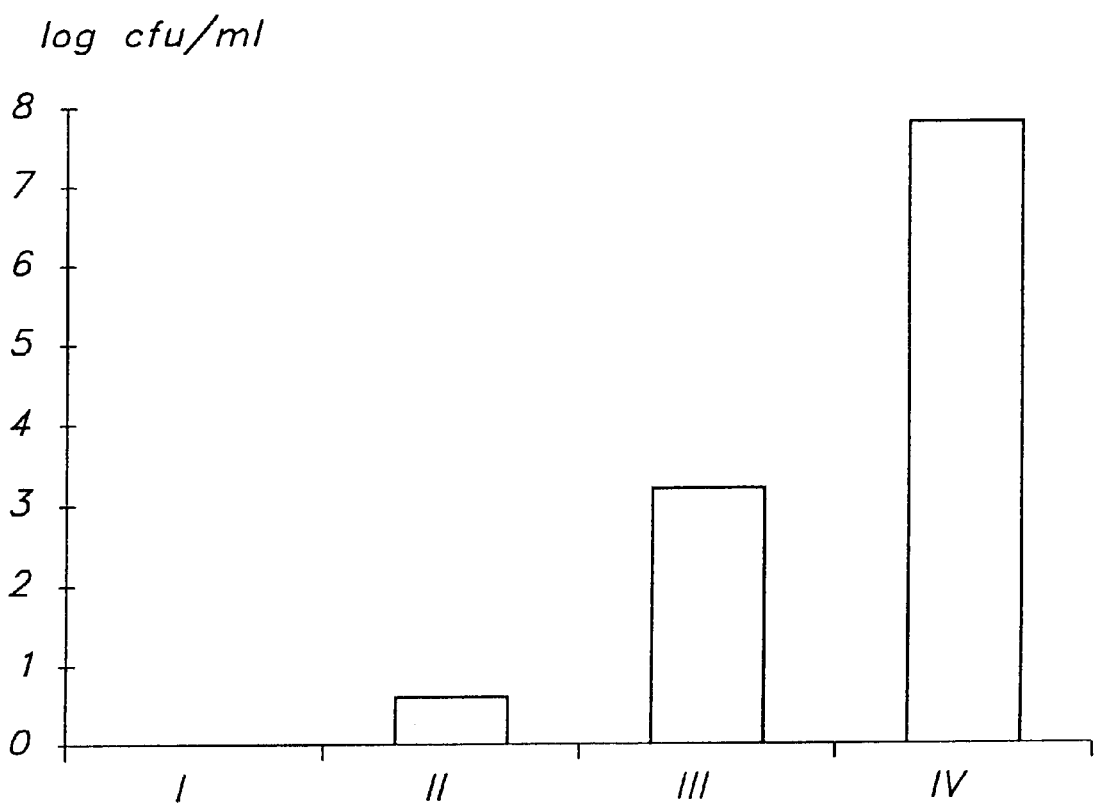
FIG. 6 shows the number of removed cells from a biofilm on a steel surface when cleaned with i) no enzyme, II) 100 ppm Bio-Cip membrane, III) 1000 ppm Bio-Cip membrane and IV) 100 ppm Bio-Cip membrane and 10 mg/L 2,6-β-D-fructan hydrolase of the mature part of SEQ ID No:1.

BioCip-membrane also removes biofilm from the steel surface, but when combining BioCip-membrane with 2,6-β-D-fructan hydrolase, the removal was significantly increased. FIG. 6 shows log cfu/ml, i.e. the logarithm to the number of cells per ml cleaning solution removed/released from a biofilm evaluated by conductance measurements on the biofilm cells remaining on the steel surface after cleaning the biofilm with I) no enzyme, II) 100 ppm Bio-Cip membrane, III) 1000 ppm Bio-Cip membrane and IV) 100 ppm Bio-Cip membrane and 10 mg/l 2,6-β-D-fructan hydrolase. A huge synergistic effect was seen when cleaning with both Bio-Cip membrane and 2,6-β-D-fructan hydrolase.

The 2,6-β-D-fructan hydrolase has shown to be an important enzyme activity for biofilm degradation, and the overall biofilm degradation of complex microbial biofilms can be further increased if 2,6-β-D-fructan hydrolase is combined with a mix of different enzymes.

Example 8

Levanase activity of Paenibacillus species was evaluated on agar plates made of ten times diluted TY-medium supplemented with stained levan and incubated overnight at 37° C. For colonies expressing the 2,6-β-D-fructan hydrolase clearing zones (decoloration of the stained levan) appeared. The following results were obtained:

| Organism | levanase activity |
|---|---|
| *Paenibacillus amylolyticus* DSM 12458 | + |
| *Paenibacillus pabuli* DSM 13026 | + |
| *Paenibacillus macerans* DSM 13025 | + |

All three strains of Paenibacillus expressed polypeptides having 2,6-β-D-fructan hydrolase activity.

Example 9

Cloning of the SEQ ID No:2 Encoding 2,6-β-D-fructan Hydrolase into *Bacillus subtilis* and Purification of the 2,6-β-D-fructan Hydrolase The 2,6-β-D-fructan,hydrolase encoding DNA sequence SEQ ID No:2 was PCR amplified using the PCR primer set consisting of these two oligo nucleotides:

Lev-amy.upper.PstI
5'-CAT TCT GCA GCA GCG GCG GCT ATG GCT GTA CTT GC-3'
Lev-amy.lower.BglII
5'-CGC GGA TCC AGA TCT TAC ATG GAG TCC AAG CTT TC-3'

Restriction sites PstI and BglII are underlined Chromosomal DNA isolated from *Paenibacillus amylolyticus* DSM 12458 was used as template in a PCR reaction using Amplitaq DNA Polymerase (Perkin Elmer) according to manufacturers instructions. The PCR reaction was set up in PCR buffer (10 mM Tris-HCl, pH 8.3, 50 mM KCl, 1.5 mM $MgCl_2$, 0.01% (w/v) gelatin) containing 200 µM of each dNTP, 2.5 units of AmpliTaq polymerase (Perkin-Elmer, Cetus, USA) and 100 pmol of each primer. The PCR reactions was performed using a DNA thermal cycler (Landgraf, Germany). One incubation at 94° C. for 1 min followed by thirty cycles of PCR performed using a cycle profile of denaturation at 94° C. for 30 sec, annealing at 60° C. for 1 min, and extension at 72° C. for 2 min. Five-µl aliquots of the amplification product was analysed by electrophoresis in 0.7% agarose gels (NuSieve, FMC)

The PCR products generated as described above were purified using QIAquick PCR purification kit (Qiagen, USA) according to the manufacturer's instructions. The purified DNA was eluted in 50 µl of 10 mM Tris-HCl, pH 8.5. pMOL944 (described supra) was digested with PstI and Bcl1, the purified PCR fragment was digested with PstI and HindIII (this fragment covering the coding sequence until the HindIII site) and plasmid pLiH937 from strain DSM 12406 digested with HindIII-BglII (this fragment covering the rest of the encoding sequence) electrophoresed in 0.8% low gelling temperature agarose (SeaPlaque GTG, FMC) gels, the relevant fragments were excised from the gels, and purified using QIAquick Gel extraction Kit (Qiagen, USA) according to the manufacturer's instructions. The isolated PCR DNA fragment and the 2.3 kb HindIII-BglII fragment from pLiH938 (see DNA sequence of invention) were then ligated to the PstI-Bcl I digested and purified pMOL944. The ligation was performed overnight at 16° C. using 0.5 µg of each DNA fragment, 1 U of T4 DNA ligase and T4 ligase buffer (Boehringer Mannheim, Germany).

The ligation mixture was used to transform competent B. subtilis SHa273. The transformed cells were plated onto LBPG-10 µg/ml of Kanamycin-agar plates. After 18 hours incubation at 37° C. colonies were seen on plates. Several clones were analyzed by isolating plasmid DNA from overnight culture broth.

One such positive clone was restreaked several times on agar plates as used above, this clone was called LiH1528 The clone LiH1528 was grown overnight in TY-10 µg/ml Kanamycin at 37° C., and next day 1 ml of cells were used to isolate plasmid from the cells using the Qiaprep Spin Plasmid Miniprep Kit #27106 according to the manufacturers recommendations for *B. subtilis* plasmid preparations.

The clone LiH 1528 was grown in 200 ml BPX media with 15 µg/ml of Kanamycin in 500 ml two baffled shake-flasks for 4–5 days at 37° C. at 300 rpm.

200 ml of the shake flask culture fluid of the clone LiH1528 was collected and centrifuged at 15000 rpm for 20 minutes in 50 ml tubes.

The supernatants were filtered through a Seitz K250 filter plate followed by a Seitz EKS filter plate to remove the production organism completely. Solid ammonium sulfate was added to the filtrate to 1.8M final concentration and the filtrate was applied to a SOURCE Phenyl column (Amersham Pharmacia Biotech) equilibrated in 10 mM $KH_2PO_4$/NaOH, 1.8 M $(NH_4)_2SO_4$, pH 7. After washing the column with the equilibration buffer, the column was eluted with a linear decreasing ammonium sulfate gradient (1.8→0 M). Fractions from the column were checked for levanase activity and active fractions were pooled and concentrated on a Amicon ultrafiltration cell equipped with a 10 kDa cut-off regenerated cellulose membrane. The concentrated enzyme was fractionated on a Superdex200 HR16/60 column (Amersham Pharmacia Biotech) equilibrated in 25 mM HEPES/NaOH, 100 mM NaCl, pH 8.0. Fractions from the column were checked for levanase activity and active fractions were purity checked on a SDS-PAGE gel. Pure fractions were pooled as purified levanase. The following N-terminal sequence of the purified protein was determined: Ser(54)-Ala-Ser-Lys-Ser-Asn-Thr-Asn-Leu-Ile-Gly-Trp-Gln-Val-Lys-Gly-Lys-Gly-; by Edman degradation of the electroblottet enzyme as known in the art.

Example 10

The 2,6-β-D-fructan hydrolase of SEQ ID No:1 was tested for activity in toothpaste using a spot test on plates containing stained levan. Samples of different tooth pastes in different concentrations containing difference amounts of 2,6-β-D-fructan hydrolase was places on the stained levan plates and clearing zone was measured after, 7 hours incubation at 37° C. showing presence of active 2,6-β-D-fructan hydrolase. The size of the clearing zone was dependent on the amount of 2,6-β-D-fructan hydrolase in the sample. The activity is independent of the concentration of toothpaste in the samples (i.e. similar diameter with increasing toothpaste concentration). The levanase is thus active in a toothpaste formulation.

Figure 7:
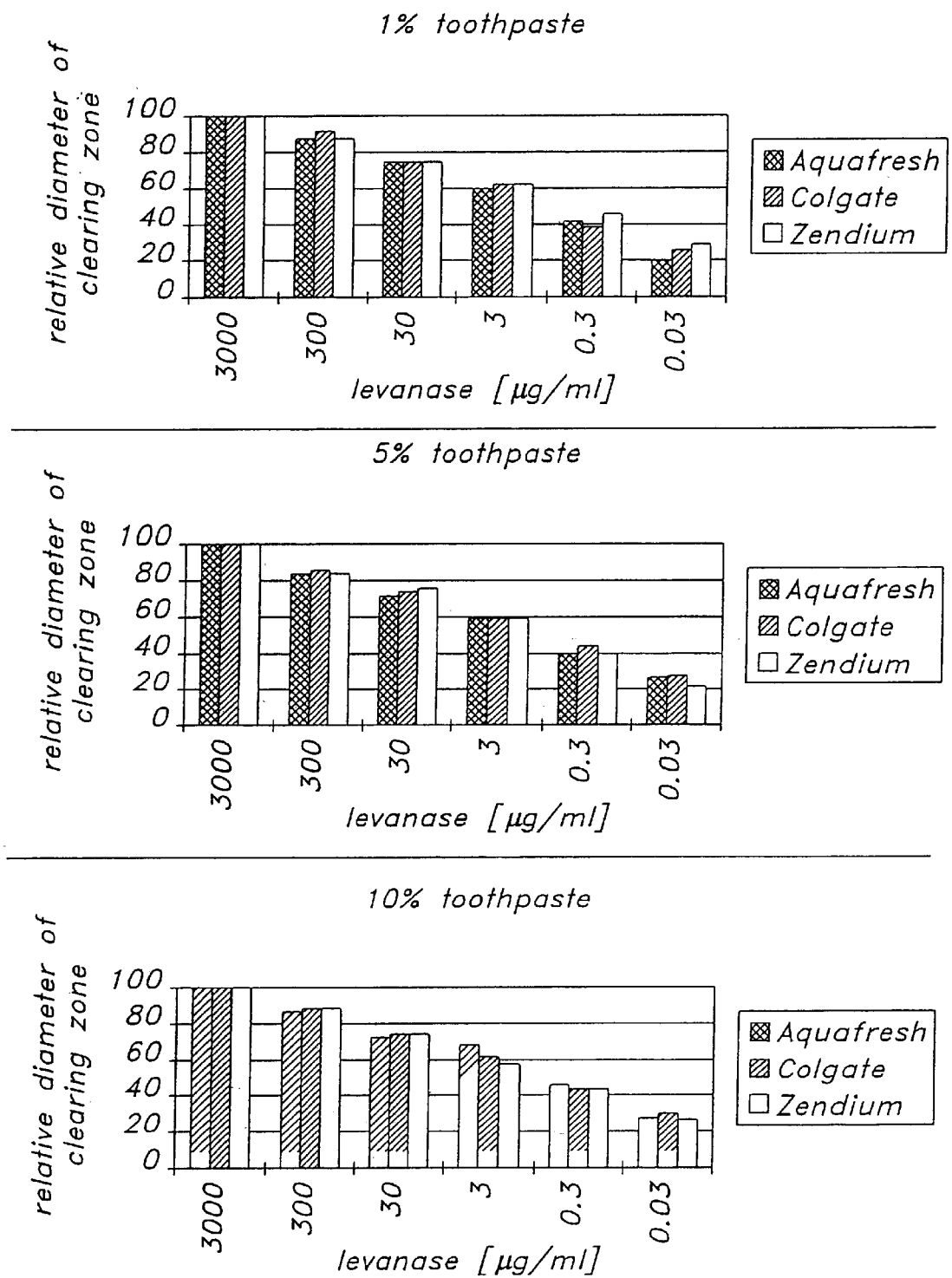
FIG. 7 shows activity of 2,6-β-D-fructan hydrolase in diluted tooth pastes.

The following tooth pastes was used:

Commercial Aquafresh 'Fresh mint/triple protection' (SmithKlime Beecham Consumer Health Care Ballerup, Denmark). Commercial Colgate 'Micro-formula/tandsten kontrol' (Colgate
Palmolive Dk-2600 Glostrup, Denmark).
Commercial Zendium: 'Cool Mint med xylitol' (Blumøller A/S Dk-5100 Odense C, Denmark). The results are shown in FIG. 7.

Example 11

Figure 8:
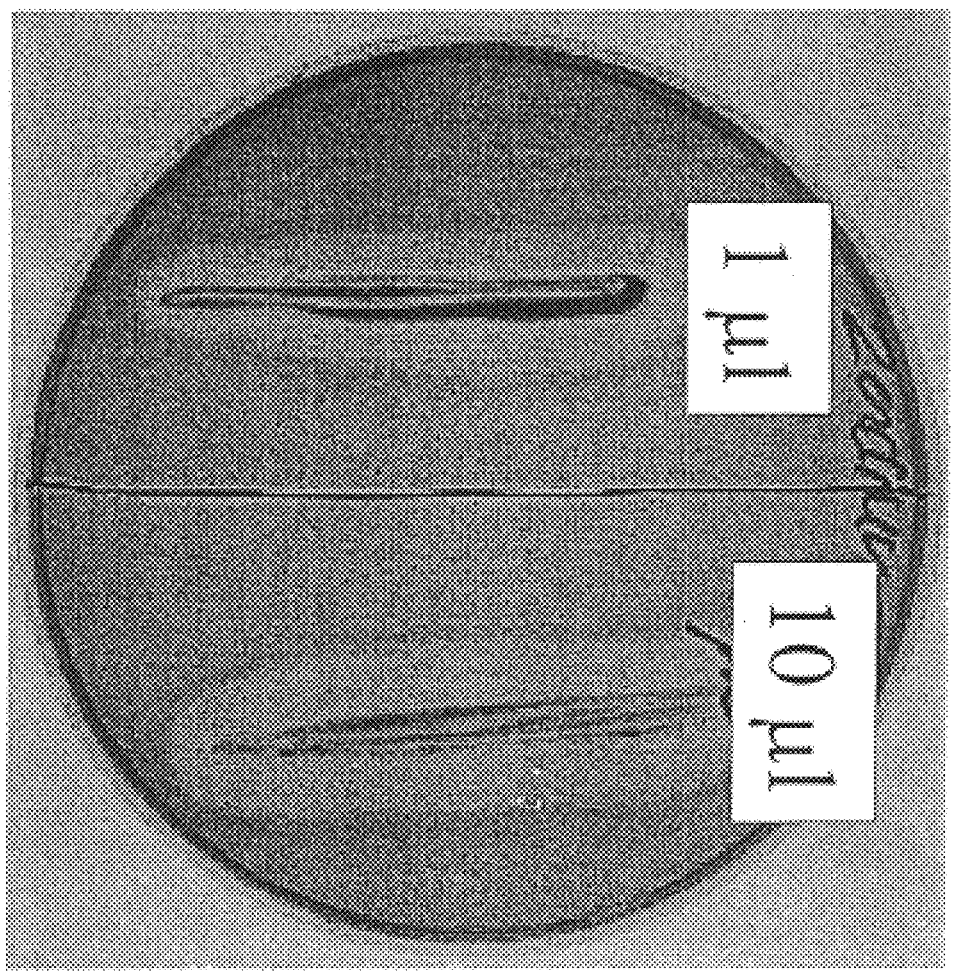
FIG. 8 shows activity of 2,6-β-D-fructan hydrolase undiluted tooth pastes.

2,5 g of the undiluted Zendium tooth paste of example 10 was mixed with 1 µl or 10 µl 2,6-β-D-fructan hydrolase of the mature part of SEQ ID No:1, and applied to plates containing stained levan and kept overnight at 37° C. temperature. The clearing zones that appeared surrounding the smear of toothpaste showed in FIG. 8, shows that the 2,6-β-D-fructan hydrolase is active after overnight incubation, and shows that the enzyme is stabile and active in an undiluted toothpaste formulation.

What is claimed is:

1. An isolated nucleic acid sequence encoding a polypeptide having 2,6-beta-D-fructan hydrolase activity, comprising a nucleic acid sequence encoding:
   a polypeptide having an amino acid sequence of amino acids 32 to 923 SEQ ID NO:1.

2. An isolated nucleic acid sequence encoding a polypeptide having 2,6-beta-D-fructan hydrolase activity, comprising a nucleic acid sequence encoding:
   an allelic variant of a polypeptide having an amino acid sequence which has at least 90% identity to amino acids 32 to 923 of SEQ ID NO:1.

3. An isolated nucleic acid sequence encoding a polypeptide having 2,6-beta-D-fructan hydrolase activity, comprising:
   a nucleic acid sequence which hybridizes under high stringency conditions with (i) nucleotides 94 to 2769 of SEQ ID NO:2 (ii) the cDNA sequence comprising nucleotides 94 to 2769 of SEQ ID NO:2 or (iii) a complementary strand of (i) or (ii); wherein the hybridization conditions comprises hybridization at 42° C. in a solution comprising 5×SSPE, 200 ug/ml sheared and denatured salmon sperm DNA, and 0.3% SDS followed by washing at 65° C. in a solution comprising 2×SSC and 0.2% SDS.

4. An isolated nucleic acid sequence encoding a polypeptide having 2,6-beta-D-fructan hydrolase activity, comprising the nucleic acid sequence inserted into plasmid pSJ1678 present in *E. coli* DSM 12406 or the nucleotide sequence inserted into plasmid pSJ1678 present in *E. coli* DSM 13028 or the nucleotide sequence inserted into plasmid pSJ1678 present in *E. coli* DSM 13029.

5. A nucleic acid construct comprising the nucleic acid sequence of claim 1 operably linked to one or more control sequences that direct the production of the nucleic acid sequence in a host cell.

6. A recombinant expression vector comprising the nucleic acid construct of claim 5.

7. A recombinant expression host cell comprising the nucleic acid construct of claim 5.

8. A nucleic acid construct comprising the nucleic acid sequence of claim 2 operably linked to one or more control sequences that direct the production of the nucleic acid sequence in a host cell.

9. A recombinant expression vector comprising the nucleic acid construct of claim 8.

10. A recombinant expression host cell comprising the nucleic acid construct of claim 8.

11. A nucleic acid construct comprising the nucleic acid sequence of claim 3 operably linked to one or more control sequences that direct the production of the nucleic acid sequence in a host cell.

12. A recombinant expression vector comprising the nucleic acid construct of claim 11.

13. A recombinant expression host cell comprising the nucleic acid construct of claim 11.

14. A nucleic acid construct comprising the nucleic acid sequence of claim 4 operably linked to one or more control sequences that direct the production of the nucleic acid sequence in a host cell.

15. A recombinant expression vector comprising the nucleic acid construct of claim 14.

16. A recombinant expression host cell comprising the nucleic acid construct of claim 14.

* * * * *